(12) United States Patent
Haynes et al.

(10) Patent No.: US 10,092,638 B2
(45) Date of Patent: Oct. 9, 2018

(54) GP120 IMMUNOGENS AND METHODS INDUCING NEUTRALIZING ANTIBODIES TO HUMAN IMMUNODEFICIENCY VIRUS

(71) Applicants: DUKE UNIVERSITY, Durham, NC (US); Children's Medical Center Corporation, Boston, MA (US)

(72) Inventors: Barton F. Haynes, Durham, NC (US); Garnett Kelsoe, Durham, NC (US); Stephen Harrison, Boston, MA (US); Thomas B. Kepler, Boston, MA (US)

(73) Assignees: DUKE UNIVERSITY, Durham, NC (US); CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 14/349,539

(22) PCT Filed: Oct. 3, 2012

(86) PCT No.: PCT/US2012/000442
§ 371 (c)(1),
(2) Date: Apr. 3, 2014

(87) PCT Pub. No.: WO2013/052095
PCT Pub. Date: Apr. 11, 2013

(65) Prior Publication Data
US 2014/0341949 A1 Nov. 20, 2014

Related U.S. Application Data

(60) Provisional application No. 61/708,503, filed on Oct. 1, 2012, provisional application No. 61/542,469, filed on Oct. 3, 2011.

(51) Int. Cl.
A61K 39/12 (2006.01)
A61K 39/21 (2006.01)
(Continued)

(52) U.S. Cl.
CPC .............. *A61K 39/21* (2013.01); *A61K 39/12* (2013.01); *C07K 16/1063* (2013.01); *C12N 7/00* (2013.01);
(Continued)

(58) Field of Classification Search
None
See application file for complete search history.

(56) References Cited

U.S. PATENT DOCUMENTS 5,858,366 A 1/1999 Sodroski et al.
6,042,836 A 3/2000 Berman et al.
(Continued)

FOREIGN PATENT DOCUMENTS

WO WO-1990/006358 A1 6/1990
WO WO-199713852 A1 4/1997
(Continued)

OTHER PUBLICATIONS

Ma et al., "Envelope Deglycosylation Enhances Antigenicity of HIV-1 gp41 Epitopes for Both Broad Neutralizing Antibodies and Their Unmutated Ancestor Antibodies," PLOS Pathogens, vol. 7, Issue 9: e1002200 (1-16) (2011).*
(Continued)

*Primary Examiner* — Janet L Andres
*Assistant Examiner* — M Franco G Salvoza
(74) *Attorney, Agent, or Firm* — Wilmer Cutler Pickering Hale and Dorr LLP

(57) ABSTRACT

The present invention relates, in general, to an HIV-1 vaccine and, in particular, to a B cell lineage-based vaccination protocol.

17 Claims, 9 Drawing Sheets

Specification includes a Sequence Listing.

(51) Int. Cl.
C07K 16/10 (2006.01)
C12N 7/00 (2006.01)
G06F 19/12 (2011.01)
A61K 39/00 (2006.01)

(52) U.S. Cl.
CPC .... G06F 19/12 (2013.01); A61K 2039/55511 (2013.01); A61K 2039/70 (2013.01); C12N 2740/16034 (2013.01); C12N 2740/16134 (2013.01); C12N 2770/00034 (2013.01)

(56) References Cited

U.S. PATENT DOCUMENTS

| | | |
|---|---|---|
| 6,806,055 B2 | 10/2004 | Berman et al. |
| 7,847,085 B2 | 12/2010 | Zolla-Pazner et al. |
| 7,951,377 B2 | 5/2011 | Korber et al. |
| 8,048,431 B2 | 11/2011 | Haynes |
| 8,071,107 B2 | 12/2011 | Haynes et al. |
| 8,092,813 B1* | 1/2012 | Novicki ............ A61K 39/39 424/278.1 |
| 8,119,140 B2 | 2/2012 | Korber et al. |
| 2002/0106629 A1 | 8/2002 | Murphy et al. |
| 2004/0052821 A1 | 3/2004 | Berman |
| 2005/0025779 A1 | 2/2005 | Berman et al. |
| 2009/0198042 A1* | 8/2009 | Korber ............ A61K 39/21 530/350 |
| 2011/0044994 A1 | 2/2011 | Chan-Hui et al. |
| 2011/0195090 A1 | 8/2011 | Dimitrov |
| 2012/0167237 A1 | 6/2012 | Bradley et al. |
| 2012/0177681 A1* | 7/2012 | Singh ............ A61K 31/661 424/193.1 |
| 2012/0308593 A1 | 12/2012 | Tartaglia et al. |
| 2012/0321699 A1 | 12/2012 | Haynes et al. |
| 2013/0251726 A1* | 9/2013 | Mascola ............ C07K 16/1063 424/142.1 |
| 2014/0205607 A1 | 7/2014 | Mascola et al. |
| 2014/0221625 A1 | 8/2014 | Haynes et al. |
| 2014/0248301 A1 | 9/2014 | Haynes et al. |
| 2014/0248311 A1* | 9/2014 | Kim ............ A61K 39/21 424/208.1 |
| 2015/0246111 A1 | 9/2015 | Berman et al. |
| 2016/0271244 A1 | 9/2016 | Haynes et al. |

FOREIGN PATENT DOCUMENTS

| | | |
|---|---|---|
| WO | WO 01-06838 | 8/2001 |
| WO | WO-2001/060838 A2 | 8/2001 |
| WO | WO-2005028625 A2 | 3/2005 |
| WO | WO-2010/019262 | 2/2010 |
| WO | WO 2011/106100 A2 | 9/2011 |
| WO | WO-2012/071521 A2 | 5/2012 |
| WO | WO-2013/006688 | 1/2013 |
| WO | WO-2013052095 A2 | 4/2013 |
| WO | WO-2014124156 A1 | 8/2014 |
| WO | WO-2015/143193 A1 | 9/2015 |

OTHER PUBLICATIONS

Korber et al., Sequence 119, U.S. Pat. No. 7,951,377 (2011).*
Korber et al., Sequence 120, U.S. Pat. No. 7,951,377 (2011).*
Korber et al., Sequence 219, U.S. Pat. No. 7,951,377 (2011).*
Pancera M et al., Crystal structure of PG16 and Chimeric Dissection with Somatically Related PG9: Structure-Function Analysis of Two Quaternary-Specific Antibodies that Effectively Neutralize HIV-1. J Virol. Aug. 2010;84(16), p. 8098-8110 (13 pages).
International Search Report for PCT/US2012/000442, dated Mar. 28, 2013, Han, In Ho.
Written Opinion of the International Searching Authority for PCT/US2012/000442, dated Mar. 28, 2013, Han, In Ho.
Wu, X. et al., Rational Design of Envelope Identifies Broadly Neutralizing Human Monoclonal Antibodies to HIV-1, Science, (Aug. 13, 2010), vol. 329, pp. 856-861.
Wu, X. et al., Supporting Online Materials for Rational Design of Envelope Identifies Broadly Neutralizing Human Monoclonal Antibodies to HIV-1, Science, (Aug. 13, 2010), vol. 329, 35 pages.
Haynes, B.F. et al., "Antibody polyspecificity and neutralization of HIV-1: A hypothesis", Human Antibodies, (2005), vol. 14, pp. 59-67.
Haynes, B.F. et al., "B-cell-lineage immunogen design in vaccine development with HIV-1 as a case study", Nature Biotechnology, (May 5, 2012), vol. 30, pp. 423-433.
Fleishman et al: "Computational Design of Proteins Targeting the Conserved Stem Region of Influenza Hemagglutinin", Science, vol. 332, No. 6031, May 13, 2011, pp. 816-821.
European Search Report dated Apr. 22, 2015 in European Application No. 12837722.3, 6 pages.
Haynes et al, "B-cell-lineage immunogen design in vaccine development with HIV-1 as a case study", Nature Biotechnology, May 2012, vol. 30, No. 5, pp. 423-433.
Bonsignori et al, "Analysis of a Clonal Lineage of HIV-1 Envelope V2/V3 Conformational Epitope-Specific Broadly Neutralizing Antibodies and Their Inferred Unmutated Common Ancestors", Journal of Virology, Oct. 2011, vol. 85, No. 19, pp. 9998-10009 & Supplemental Material (26 pages).
Alt, F. W., et al., "Development of the primary antibody repertoire," Science, vol. 238, No. 4830, pp. 1079-1087 (Nov. 20, 1987).
Chen, C., et al., "Deletion and editing of B cells that express antibodies to DNA," J. Immunol., vol. 152, pp. 1970-1982 (1994).
Clarke, S. H., et al., "V region gene usage and somatic mutation in the primary and secondary responses to influenza virus hemagglutinin," J. Immunol., vol. 144, No. 7, pp. 2795-2801 (Apr. 1, 1990).
Dell'Era, L., et al., "Immunogenicity, safety and tolerability of MF59-adjuvanted seasonal influenza vaccine in children with juvenile idiopathic arthritis," Vaccine, vol. 30, pp. 936-940 (Dec. 3, 2011).
Ehlich, A., et al., "Analysis of the B-cell progenitor compartment at the level of single cells," Curr. Biol., vol. 4, No. 7, pp. 573-583 (1994).
Goodnow, C. C., "Transgenic mice and analysis of B-cell tolerance," Annu. Rev. Immunol., vol. 10, pp. 489-518 (1992).
Hardy, R. R. and Hayakawa, K., "B cell development pathways," Annu. Rev. Immunol., vol. 19, pp. 595-621 (2001).
Haynes, B. F., et al., "HIV Type 1 V3 Region Primer-Induced Antibody Suppression is Overcome by Administration of C4-V3 Peptides as a Polyvalent Immunogen," AIDS Res. Human Retroviruses, vol. 11, No. 2, pp. 211-221 (1995).
Hessell, A. J., et al., "Fc receptor but not complement binding is important in antibody protection against HIV," Nature, vol. 449, pp. 101-104, 5 pages (Sep. 6, 2007).
Hilleman, Maurice R., "Overview of the needs and realities for developing new and improved vaccines in the 21st century," Intervirology, vol. 45, pp. 199-211 (2002).
Kelsoe, Garnett, "In situ studies of the germinal center reaction," Adv. Immunol., vol. 60, pp. 267-288, 24 pages (1995).
Kepler, Thomas B., "Codon bias and plasticity in immunoglobulins," Molecular Biology and Evolution, vol. 14, No. 6, pp. 637-643 (1997).
Leroux-Roels, I., et al., "Strong and persistent CD4+ T-cell response in healthy adults immunized with a candidate HIV-1 vaccine containing gp120, Nef and Tat antigens formulated in three Adjuvant Systems," Vaccine, vol. 28, pp. 7016-7024 (Aug. 20, 2010).
Nemazee, D. A. and Buerki, K., "Clonal deletion of B lymphocytes in a transgenic mouse bearing anti-MHC class I antibody genes," Nature, vol. 337, pp. 562-566 (Feb. 9, 1989).
Pulendran, B. et al., "Soluble Antigen Can Cause Enhanced Apoptosis of Germinal-Centre B Cells," Nature, 375, pp. 331-334 (May 25, 1995).
Rajewsky, Klaus, "Clonal Selection and Learning in the Antibody System," Nature, vol. 381, pp. 751-758 (Jun. 27, 1996).
Rogozin, I. B., et al., "Somatic Hypermutagenesis in Immunoglobulin Genes: II. Influence of Neighbouring Base Sequences on Mutagenesis," Biochimica et Biophysica Acta (BBA)—Gene Structure and Expression, vol. 1171, pp. 11-18 (1992).

(56) References Cited

OTHER PUBLICATIONS

Rolink, A. G., et al., "Characterization of Immature B Cells by a Novel Monoclonal Antibody, by Turnover and by Mitogen Reactivity," Eur. J. Immunol., vol. 28, pp. 3738-3748 (Nov. 1998).
Rolland M., et al., "Increased HIV-1 vaccine efficacy against viruses with genetic signatures in Env V2," Nature, vol. 490, pp. 417-421 (Oct. 18, 2012).
Schlissel, M. S., et al., "Activation of Immunoglobulin Kappa Gene Rearrangement Correlates with Induction of Germline Kappa Gene Transcription," Cell, vol. 58, pp. 1001-1007 (Sep. 8, 1989).
Shih, T-A. Y., et al., "Role of BCR Affinity in T Cell-Dependent Antibody Responses in Vivo," Nat. Immunol., vol. 3, No. 6, pp. 570-575 (May 20, 2002).
Shokat, K. M., et al., "Antigen-Induced B-Cell Death and Elimination during Germinal-Centre Immune Responses," Nature, vol. 375, pp. 334-338 (May 25, 1995).
Thomas, S. J. and Endy, T. P., "Critical Issues in Dengue Vaccine Development," Curr. Opin. Infect. Dis., vol. 24, No. 5, 17 pages—entire document (Oct. 2011 ).
Walker, B. D. and Burton, D. R., "Toward an AIDS Vaccine," Science, vol. 320, pp. 760-764 (May 9, 2008).
Wardemann, H., et al,. "Predominant Autoantibody Production by Early Human B cell Precursors," Science, vol. 301, pp. 1374-1377 (Aug. 14, 2003).
Wardemann, H. and Nussenzweig, M. C., "B-cell Self-Tolerance in Humans," Adv. Immunol., vol. 95, Chapter 3, pp. 83-110 (2007).
Wei, X., et al., "Antibody Neutralization and Escape by HIV-1", Nature, vol. 422, pp. 307-312 (Mar. 20, 2003).
Adams, E., et al., "Intrinsic B-cell hyporesponsiveness accounts for self-tolerance in lysozyme/anti-lysozyme double-transgenic mice," Proc. Natl. Acad. Sci. USA, vol. 87, pp. 5687-5691 (Aug. 1990).
Alam, S. M., et al., "Differential reactivity of germ line allelic variants of a broadly neutralizing HIV-1 antibody to a gp41 fusion intermediate conformation," Journal of Virology, vol. 85, No. 22, pp. 11725-11731 (Nov. 2011).
Alam, S. M., et al., "Role of HIV membrane in neutralization by two broadly neutralizing antibodies," Proc. Natl. Acad. Sci. USA, vol. 106, No. 48, pp. 20234-20239 (Dec. 1, 2009).
Alt, F. W., et al., "Ordered rearrangement of immunoglobulin heavy chain variable region segments," EMBO J., vol. 3, No. 6, pp. 1209-1219 (1984).
Batista, F. D. & Neuberger, M.S., "Affinity dependence of the B cell response to antigen: a threshold, a ceiling, and the importance of off-rate," Immunity, vol. 8, pp. 751-759 (Jun. 1998).
Boekel, E., et al., "Changes in the $V_H$ gene repertoire of developing precursor B lymphocytes in mouse bone marrow mediated by the pre-B cell receptor," Immunity, vol. 7, pp. 357-368 (Sep. 1997).
Burton, D. R., et al., "Antibody vs. HIV in a clash of evolutionary titans," Proc. Natl. Acad. Sci. USA, vol. 102, No. 42, pp. 14943-14948, (Oct. 18, 2005).
Calarese, D. A., et al., "Dissection of the carbohydrate specificity of the broadly neutralizing anti-HIV-1 antibody 2G12," Proc. Natl. Acad. Sci. USA, vol. 102, No. 38, pp. 13372-13377, 9 pages (Sep. 20, 2005).
Carsetti, R., et al., "Transitional B cells are the target of negative selection in the B cell compartment," J. Exp. Med., vol. 181, pp. 2129-2140 (Jun. 1995).
Changela, A., et al., "Crystal structure of human antibody 2909 reveals conserved features of quaternary structure-specific antibodies that potently neutralize HIV-1," J. Virol., vol. 85, No. 6, pp. 2524-2535, 16 pages (Mar. 2011).
Clarke, S. H., et al., "Inter- and intraclonal diversity in the antibody response to influenza hemagglutinin," J. Exp. Med., vol. 161, pp. 687-704 (Apr. 1985).
Crotty, Shane, "Follicular helper CD4 T cells ($T_{FH}$)," Annu. Rev. Immunol., vol. 29, pp. 621-663 (2011).
Verkoczy, L., et al., "Autoreactivity in an HIV-1 broadly reactive neutralizing antibody variable region heavy chain induces immunologic tolerance," Proc. Natl. Acad. Sci. USA, vol. 107, pp. 181-186 (2010).

Dal Porto, J. M., et al., "Antigen drives very low affinity B cells to become plasmacytes and enter germinal centers," J. Immunol., vol. 161, pp. 5373-5381 (1998).
Dal Porto, J. M., et al., "Very low affinity B cells form germinal centers, become memory B cells, and participate in secondary immune responses when higher affinity competition is reduced," J. Exp. Med., vol. 195, No. 9, pp. 1215-1221, consisting of 9 pages total (May 6, 2002).
Di Noia, J. M. & Neuberger, M.S., "Molecular Mechanisms of Antibody Somatic Hypermutation," Annual Review of Biochemistry, vol. 76, pp. 1-22 (2007).
Dimitrov, Dimiter S., "Therapeutic antibodies, vaccines and antibodyomes," mAbs, vol. 2, No. 3, pp. 347-356 (May/Jun. 2010).
Ekiert, D. C., et al., "Antibody recognition of a highly conserved influenza virus epitope: implications for universal prevention and therapy," Science, vol. 324, No. 5924, pp. 246-251 (Apr. 10, 2009), Author Manuscript consisting of 9 pages total.
Frey, G., et al., "A fusion-intermediate state of HIV-1 gp41 targeted by broadly neutralizing antibodies," Proc. Natl. Acad. Sci. USA, vol. 105, No. 10, pp. 3739-3744 (Mar. 11, 2008).
Gray, E. S., et al., "Isolation of a monoclonal antibody that targets the alpha-2 helix of gp120 and represents the initial autologous neutralizing-antibody response in an HIV-1 subtype C-infected individual," J. Viral., vol. 85, No. 15, pp. 7719-7729, consisting of 15 pages in total (Aug. 2011).
Gray, E. S., et al., "The neutralization breadth of HIV-1 develops incrementally over four years and is associated with $CD4^+$ T cell decline and high viral load during acute infection," J. Viral., vol. 85, No. 10, pp. 4828-4840 (May 2011).
Gu, H., et al., "Most peripheral B cells in mice are ligand selected," J. Exp. Med., vol. 173, pp. 1357-1371 (Jun. 1991).
Halliday, J., et al., "Vaccination for hepatitis C virus: closing in on an evasive target," Expert Rev. Vaccines, vol. 10, No. 5, pp. 659-672, 20 pages (May 2011), Author Manuscript consisting of 20 pages total.
Han, S., et al., "In situ studies of the primary immune response to (4-hydroxy-3-nitrophenyl)acetyl IV. Affinity-dependent, antigen-driven B cell apoptosis in germinal centers as a mechanism for maintaining self-tolerance," J. Exp. Med., vol. 182, No. 6, pp. 1635-1644 (Dec. 1, 1995).
Hardy, R. R., et al., "Resolution and characterization of pro-B and pre-pro-B cell stages in normal mouse bone marrow," J. Exp. Med., vol. 173, pp. 1213-1225 (1991).
Hayakawa, K., et al., "Positive selection of natural autoreactive B cells," Science, vol. 285, pp. 113-116 (1999).
Haynes, B. F., et al., "Cardiolipin polyspecific autoreactivity in two broadly neutralizing HIV-I antibodies," Science, vol. 308, pp. 1906-1908 (Jun. 24, 2005).
Haynes, B. F., et al., "Immune-Correlates Analysis of an HIV-1 Vaccine Efficacy Trial," The New England Journal of Medicine, vol. 366, No. 14, pp. 1275-1286 (Apr. 5, 2012).
Hessell, A. J., et al., "Broadly neutralizing human anti-HIV antibody 2G12 is effective in protection against mucosal SHIV challenge even at low serum neutralizing titers," PLoS Pathog., vol. 5, Issue 5, e1000433, pp. 1-9 (May 2009).
Hessell, A. J., et al., "Broadly neutralizing monoclonal antibodies 2F5 and 4E10 directed against the human immunodeficiency virus type 1 gp41 membrane-proximal external region protect against mucosal challenge by simian-human immunodeficiency virus SHIVBa-L," J. Viral., vol. 84, No. 3, pp. 1302-1313 (Feb. 2010).
Hessell, A. J., et al., "Effective, low-titer antibody protection against low-dose repeated mucosal SHIV challenge in macaques," Nature Med., vol. 15, No. 8, pp. 951-954, consisting of 5 pages total (Aug. 2009).
Hioe, C. E., et al., "Anti-V3 Monoclonal Antibodies Display Broad Neutralizing Activities against Multiple HIV-1 Subtypes", PLOS One, vol. 5, No. 4, e10254, 14 pages (Apr. 21, 2010).
International Search Report and Written Opinion issued by the European Patent Office as Searching Authority in PCT/US2014/015133, dated Apr. 2, 2014 (10 pages).

(56) References Cited

OTHER PUBLICATIONS

Karasuyama, H., et al., "The proteins encoded by the VpreB and lambda 5 pre-B cell-specific genes can associate with each other and with mu heavy chain," J. Exp. Med., vol. 172, pp. 969-972 (Sep. 1990).

Karasuyama, H., et al., "A complex of glycoproteins is associated with $V_{preB}/\lambda_5$ surrogate light chain on the surface of μ heavy chain-negative early precursor B cell lines," J. Exp. Med., vol. 178, pp. 469-478 (Aug. 1993).

Kashyap, A. K., et al., "Combinatorial antibody libraries from survivors of the Turkish H5N1 avian influenza outbreak reveal virus neutralization strategies," Proc. Natl. Acad. Sci. USA, vol. 105, No. 16, pp. 5986-5991 (Apr. 22, 2008).

Kepler, T. B. & Perelson, A. S., "Somatic hypermutation in B cells: an optimal control treatment," J. Theor. Biol., vol. 164, No. 1, pp. 37-64 (Sep. 7, 1993).

Klein, F., et al., "Antibodies in HIV-1 Vaccine Development and Therapy," Science, vol. 341, No. 6151, pp. 1199-1204 (2013), Author Manuscript consisting of 17 pages.

Levine, M. H., et al., "A B-cell receptor-specific selection step governs immature to mature B cell differentiation," Proc. Natl. Acad. Sci. USA, vol. 97, No. 6, pp. 2743-2748 (Mar. 14, 2000).

Li, Y. S., et al., "The regulated expression of B lineage associated genes during B cell differentiation in bone marrow and fetal liver," J. Exp. Med., vol. 178, pp. 951-960 (Sep. 1993).

Li, Z., et al., "A conserved degradation signal regulates RAG-2 accumulation during cell division and links V(D)J recombination to the cell cycle," Immunity, vol. 5, pp. 575-589 (Dec. 1996).

Liao, H. X., et al., "Initial antibodies binding to HIV-1 gp41 in acutely infected subjects are polyreactive and highly mutated," J. Exp. Med., pp. 1-13 (Oct. 10, 2011).

Loder, F., et al., "B cell development in the spleen takes place in discrete steps and is determined by the quality of B cell receptor-derived signals," J. Exp. Med., vol. 190, No. 1, pp. 75-89 (Jul. 5, 1999).

McElrath, M. J. & Haynes, B.F., "Induction of immunity to human immunodeficiency virus type-1 by vaccination," Immunity, vol. 33, pp. 542-554 (Oct. 29, 2010).

Meffre, E., et al., "Surrogate light chain expressing human peripheral B cells produce self-reactive antibodies," J. Exp. Med., vol. 199, No. 1, pp. 145-150 (Jan. 5, 2004).

Messmer, B. T., et al., "Multiple distinct sets of stereotyped antigen receptors indicate a role for antigen in promoting chronic lymphocytic leukemia," J. Exp. Med., vol. 200, No. 4, pp. 519-525 (Aug. 16, 2004).

Mietzner, B., et al., "Autoreactive IgG memory antibodies in patients with systemic lupus erythematosus arise from nonreactive and polyreactive precursors," Proc. Natl. Acad. Sci. USA, vol. 105, No. 28, pp. 9727-9732 (Jul. 15, 2008).

Montefiori, D. C., et al., "Magnitude and Breadth of the Neutralizing Antibody Response in the RV144 and Vax003 HIV-1 Vaccine Efficacy Trials," J. Inf. Dis., vol. 206, pp. 431-441 (Aug. 1, 2012).

Moody, M., et al., "H3N2 Influenza Infection Elicits More Cross-reactive and Less Clonally Expanded Anti-hemagglutinin Antibodies Than Influenza Vaccination," PLoS One, vol. 6, Issue 10, e25797, pp. 1-14 (Oct. 2011).

Munshaw, S. et al., "SoDA2: a Hidden Markov Model approach for identification of immunoglobulin rearrangements", Bioinformatics, vol. 26, No. 7, pp. 867-872 (2010).

Nabel, G. J. & Fauci, A. S., "Induction of unnatural immunity: prospects for a broadly protective universal influenza vaccine," Nat. Med., vol. 16, No. 12, pp. 1389-1391 (Dec. 2010).

Nemazee, D. & Weigert, M., "Revising B cell receptors," J. Exp. Med., vol. 191, No. 11, pp. 1813-1817 (Jun. 5, 2000).

Ofek, G. et al., "Elicitation of structure-specific antibodies by epitope scaffolds," Proc. Natl. Acad. Sci. USA, vol. 107, No. 42, pp. 17880-17887 (Oct. 19, 2010).

Ohno, T., et al., "A Broadly Neutralizing Monoclonal Antibody that Recognizes the $V_3$ Region of Human Immunodeficiency Virus Type 1 Glycoprotein gp120," Proc. Natl. Adac. Sci. USA, vol. 88, pp. 10726-10729 (1991).

Perez-Andres, M., et al., "Human peripheral blood B-cell compartments: a crossroad in B-cell traffic," Cytometry Part B (Clin. Cytom.), vol. 78B, Suppl. 1, pp. S47-S60 (2010).

Phillips, Robert S., "Structure, mechanism, and substrate specificity of kynureninase," Biochem. Biophys. Acta., vol. 1814, No. 11, pp. 1481-1488, Author Manuscript consisting of 19 pages total (Nov. 2011).

Plotkin, Stanley A., "Correlates of protection induced by vaccination," Clin. Vaccine Immunol., vol. 17, No. 7, pp. 1055-1065 (Jul. 2010).

Plotkin, Stanley A., "Correlates of vaccine-induced immunity," Clin. Infect. Dis., vol. 47, pp. 401-409 (2008).

Plotkin, Stanley A., "Vaccines: the fourth century," Clin, Vaccine Immunol., vol. 16, No. 12, pp. 1709-1719 (Dec. 2009).

Radic, M. et al., "B Lymphocytes May Escape Tolerance by Revising Their Antigen Receptors," J. Exp. Med., vol. 177, pp. 1165-1173 (1993).

Reth, M. et al., "Activation of V kappa Gene Rearrangement in pre-B Cells Follows the Expression of Membrane-bound Immunoglobulin Heavy Chains," EMBO J., vol. 6, No. 11, pp. 3299-3305 (1987).

Richman, D. D. et al., "Rapid Evolution of the Neutralizing Antibody Response to HIV Type 1 Infection," Proc. Natl. Acad. Sci. USA, vol. 100, No. 7, pp. 4144-4149 (2003).

Scheid, J. F. et al., "Broad Diversity of Neutralizing Antibodies Isolated from Memory B Cells in HIV-Infected Individuals," Nature, vol. 458, pp. 636-640 (2009).

Schwickert, T. A. et al., "A Dynamic T Cell-Limited Checkpoint Regulates Affinity-Dependent B Cell Entry into the Germinal Center," J. Exp. Med., vol. 208, No. 6, pp. 1243-1252 (2011).

Shlomchik, M. et al., "Anti-DNA Antibodies from Autoimmune Mice Arise by Clonal Expansion and Somatic Mutation," J. Exp. Med., vol. 171, pp. 265-292 (1990).

Smith, G. P. et al., "Phage Display", Chemical Reviews, vol. 97, No. 2, pp. 391-410 (1997).

Sui, J. et al., "Structural and Functional Bases for Broad-Spectrum Neutralization of Avian and Human Influenza A Viruses," Nat. Struct. Mol. Biol., vol. 16, Issue 3, pp. 265-273 (2009), Author Manuscript consisting of 22 pages total.

Tarlinton, D. et al., "Diversity Among Memory B Cells: Origin, Consequences, and Utility", Science, vol. 341, pp. 1205-1211 (2013) consisting of 8 pages in total.

Throsby, M. et al., "Heterosubtypic Neutralizing Monoclonal Antibodies Cross—Protective against H5N1 and H1N1 Recovered from Human IgM+ Memory B Cells," PLoS One, vol. 3, Issue 12, e3942, pp. 1-15 (2008).

Tiegs, S. L., et al., "Receptor Editing in Self-Reactive Bone Marrow B Cells," J. Exp. Med., vol. 177, pp. 1009-1020 (1993).

Tiller, T. et al., "Autoreactivity in Human IgG+ Memory B Cells", Immunity, vol. 26, pp. 205-213 (2007).

Tobin, G. et al., "Subsets with Restricted Immunoglobulin Gene Rearrangement Features Indicate a Role for Antigen Selection in the Development of Chronic Lymphocytic Leukemia," Blood, vol. 104, No. 9, pp. 2879-2885 (2004).

Tomaras, G. D. et al., "Initial B-Cell Responses to Transmitted Human Immunodeficiency Virus Type 1: Virion-Binding Immunoglobulin M (IgM) and IgG Antibodies Followed by Plasma Anti-gp41 Antibodies with Ineffective Control of Initial Viremia," J. Viral., vol. 82, No. 24, pp. 12449-12463 (2008).

Tomaras, G. D. et al., "Polyclonal B Cell Responses to Conserved Neutralization Epitopes in a Subset of HIV-1 Infected Individuals," J. Virol., in press, vol. 85, No. 21, pp. 11502-11519 (2011).

Tsuiji, M. et al., "A Checkpoint for Autoreactivity in Human IgM+ Memory B Cell Development," J. Exp. Med., vol. 203, No. 2, pp. 393-400 (2006).

U.S. Appl. No. 61/542,469, filed Oct. 3, 2011 consisting of 42 pages in total.

(56) References Cited

OTHER PUBLICATIONS

Verkoczy, L. et al., "Rescue of HIV-1 Broad Neutralizing Antibody-Expressing B Cells in 2F5 $V_H$ × VL Knockin Mice Reveals Multiple Tolerance Controls.," J. Immunol., vol. 187, pp. 3785-3797 (2011).

Verkoczy, L. et al., "Role of Immune Mechanisms in Induction of HIV-1 Broadly Neutralizing Antibodies," Curr. Opin. Immunol., vol. 23, Issue 3, pp. 383-390 (2011), Author Manuscript consisting of 12 pages total.

Victora, G. D. et al., "Germinal Center Dynamics Revealed by Multiphoton Microscopy with a Photoactivatable Fluorescent Reporter," Cell, vol. 143, pp. 592-605 (2010).

Volpe, J. M., et al., "SoDA: implementation of a 3D alignment algorithm for inference of antigen receptor recombinations", Bioinformatics, vol. 22, No. 4, pp. 438-444 (2006).

Walker, L. M. et al., "A Limited Number of Antibody Specificities Mediate Broad and Potent Serum Neutralization in Selected HIV-1 Infected Individuals," PLoS Pathog., vol. 6, Issue 8, e1001028, pp. 1-14 (2010).

Walker, L. M. et al., "Broad and Potent Neutralizing Antibodies from an African Donor Reveal a New HIV-1 Vaccine Target," Science, vol. 326, Issue 5950, pp. 285-289 (2009), Author Manuscript consisting of 10 pages total.

Walker, L. M. et al., "Broad Neutralization Coverage of HIV by Multiple Highly Potent Antibodies," Nature, vol. 477, Issue 7365, pp. 466-470 (2011), Author Manuscript consisting of 14 pages total.

Wang, H. et al., "Transitional B Cells Lose Their Ability to Receptor Edit but Retain Their Potential for Positive and Negative Selection", J. Immunol., vol. 179, pp. 7544-7552 (2007).

Wang, P. et al., "A Promising General Solution to the Problem of Ligating Peptides and Glycopeptides," J. Am. Chem. Soc., vol. 132, No. 47, pp. 17045-17051 (2010), Author Manuscript consisting of 15 pages total.

Wardemann, H. et al., "Human Autoantibody Silencing by Immunoglobulin Light Chains," J. Exp. Med., vol. 200, No. 2, pp. 191-199 (2004).

Whittle, J. R. et al., "Broadly Neutralizing Human Antibody that Recognizes the Receptor-Binding Pocket of Influenza Virus Hemagglutinin," Proc. Natl. Acad. Sci. USA, vol. 108, No. 34, pp. 14216-14221 (2011).

Wrammert, J. et al., "Rapid Cloning of High-Affinity Human Monoclonal Antibodies against Influenza Virus", Nature, vol. 453, Issue 7195, pp. 667-671 (2008), Author Manuscript consisting of 15 page total.

Wu, X. et al., "Focused Evolution of HIV-1 Neutralizing Antibodies Revealed by Structures and Deep Sequencing," Science, vol. 333, No. 6049, pp. 1593-1602 (2011), Author Manuscript consisting of 17 pages total.

Xiao, X. et al., "Germline-like Predecessors of Broadly Neutralizing Antibodies Lack Measurable Binding to HIV-1 Envelope Glycoproteins: Implications for Evasion of Immune Responses and Design of Vaccine Immunogens," Biochem. Biophys. Res. Commun., vol. 390, Issue 3, pp. 404-409 (2009), Author Manuscript consisting of 14 pages total.

Xiao, X. et al., "Maturation Pathways of Cross-Reactive HIV-1 Neutralizing Antibodies," Viruses, vol. 1, pp. 802-817 (2009).

Yuan, Y. et al., "Toward Homogeneous Erythropoietin: Fine Tuning of the C-Terminal Acyl Donor in the Chemical Synthesis of the $Cys^{29}$-$Gly^{77}$ Glycopeptide Domain," J. Am. Chem. Soc., vol. 131, No. 15, pp. 5432-5437 (2009), Author Manuscript consisting of 13 pages total.

Zhang, J. et al., "Optimality of Mutation and Selection in Germinal Centers," PLoS Comput. Biol., vol. 6, Issue 6, e1000800 (2010), pp. 1-9.

Zwick, M. B. et al., "Broadly Neutralizing Antibodies Targeted to the Membrane-Proximal External Region of Human Immunodeficiency Virus Type 1 Glycoprotein gp41," J. Virol., vol. 75, No. 22, pp. 10892-10905 (2001).

Alam, S. M. et al., "Antigenicity and Immunogenicity of RV144 Vaccine AIDSVAX Clade E Envelope Immunogen is Enhanced by a gp120 N-Terminal Deletion," Journal of Virology, vol. 87, No. 3, pp. 1554-1568 (2013).

Li, Y. et al., "Control of Expression, Glycosylation, and Secretion of HIV-1 gp120 by Homologous and Heterologous Signal Sequences," Virology, pp. 266-278 (1994).

Li, Y. et al., "Effects of Inefficient Cleavage of the Signal Sequence of HIV-1 gp120 on its Association with Calnexin, Folding, and Intracellular Transport," Proc. Natl. Acad. Sci. USA, vol. 93, pp. 9606-9611 (1996).

Land, A. et al., "Folding of HIV-1 Envelope Glycoprotein Involves Extensive Isomerization of Disulfide Bonds and Conformation-Dependent Leader Peptide Cleavage," The FASEB Journal, vol. 17, pp. 1058-1067 (2003).

Berman, P. W. et al., "Expression of Membrane-Associated and Secreted Variants of gp160 of Human Immunodeficiency Virus Type 1 In Vitro and in Continuous Cell Lines", Journal of Virology, vol. 62, No. 9, pp. 3135-3142 (1988).

International Preliminary Report on Patentability for PCT/US2014/015133 dated Aug. 20, 2015 consisting of 8 pages total.

Haynes, B. F., et al., "B-cell-lineage immunogen design in vaccine development with HIV-1 as a case study," Nature Biotechnology, vol. 30, No. 5, pp. 423-433 (2012), Author Manuscript consisting of 30 pages in total.

Alam, S. M., et al., "Human Immunodeficiency Virus Type 1 gp41 Antibodies That Mask Membrane Proximal Region Epitopes: Antibody Binding Kinetics, Induction, and Potential for Regulation in Acute Infection," Journal of Virology, vol. 82, No. 1, pp. 115-125 (Jan. 2008).

Alam, S. M., et al., "The Role of Antibody Polyspecificity and Lipid Reactivity in Binding of Broadly Neutralizing Anti-HIV-1 Envelope Human Monoclonal Antibodies 2F5 and 4E10 to Glycoprotein 41 Membrane Proximal Envelope Epitopes," Journal of Immunology, 178 (7), pp. 4424-4435, Author Manuscript—25 pages (Apr. 1, 2007).

Barefoot, B., et al., "Comparison of Multiple Vaccine Vectors in a Single Heterologous Prime Boost Trial," Vaccine vol. 26, No. 48, pp. 6108-6118, Author Manuscript—23 pages (Nov. 11, 2008).

Barouch, D. H., et al. "Mosaic HIV-1 Vaccines Expand the Breadth and Depth of Cellular Immune Responses in Rhesus Monkeys," Nature Med. 16(3): pp. 319-323, Author Manuscript—15 pages (Mar. 2010).

Berman, P. W., "Development of Bivalent rpg120 Vaccines to Prevent HIV Type 1 infection," AIDS Research and Human Retroviruses, 14 (3):pp. S-277-S-289, (1998).

Berman, P. W., et al, "Development of Bivalent (B/E) Vaccines Able to Neutralize CCR5-Dependent Viruses from the United States and Thailand," Virology, vol. 265, pp. 1-9 (1999).

Billings, E. A., et al., "Surface Plasmon Resonance Analysis of Anti-gp120 V2-Specific IgG Antibodies Generated in the RV144 Thai Trial", AIDS Research and Human Retroviruses, vol. 27, No. 10, Abstracts from AIDS Vaccine Conference 2011, Bangkok, Thailand, pp. A-21 and A-22, 4 pages (Sep. 12-15, 2011).

Bonsignori, M., et al., "Isolation of CD4-Binding Site and V2/V3 Conformational (Quaternary) Broadly Neutralizing Antibodies from the Same HIV-1 Infected African Subject", AIDS Research and Human Retroviruses, vol. 27, No. 10, Abstracts from AIDS Vaccine Conference 2011, Bangkok, Thailand, p. A-120, 3 pages (Sep. 12-15, 2011).

Davenport, T., et al., "Binding Interactions Between Soluble HIV Envelope Glycoproteins and Quaternary-Structure-Specific Monoclonal Antibodies PG9 and PG16," Journal of Virology, vol. 85, No. 14, pp. 7095-7107, (Jul. 2011).

Ewing, B. and Green, P., "Base-Calling of Automated Sequencer Traces Using Phred. II. Error Probabilities," Genome Research, vol. 8, pp. 186-194, 10 pages (1998).

Ewing, B., et al., "Base-Calling of Automated Sequencer Traces Using Phred. I. Accuracy Assessment," Genome Research, vol. 8, pp. 175-185, 12 pages (1998).

Ferrari, G., et al., "An HIV-1 gp120 Envelope Human Monoclonal Antibody That Recognizes a C1 Conformational Epitope Mediates Potent Antibody-Dependent Cellular Cytotoxicity (ADCC) Activity

(56) References Cited

OTHER PUBLICATIONS and Defines a Common ADCC Epitope in Human HIV-1 Serum," Journal of Virology, vol. 85, No. 14, pp. 7029-7036 (Jul. 2011).
Finzi, A., et al., "Conformational Characterization of Aberrant Disulfide-Linked HIV-1 gp120 Dimers Secreted from Overexpressing Cells," J. Viral. Methods, vol. 168, Nos. 1-2, 155-161, Author Manuscript—15 pages (Sep. 2010).
Flynn, B. J., et al., "Immunization with HIV Gag Targeted to Dendritic Cells Followed by Recombinant New York Vaccinia Virus Induces Robust T-cell Immunity in Nonhuman Primates," Proceedings of the National Academy of Sciences, vol. 108, No. 17, pp. 7131-7136 (Apr. 26, 2011).
Flynn, et al., "Placebo-Controlled Phase 3 Trial of a Recombinant Glycoprotein 120 Vaccine to Prevent HIV-1 Infection," The Journal of Infectious Diseases, vol. 191, pp. 654-665 (Mar. 1, 2005).
Francis, D. P., et al., "Advancing AIDSVAX™ to Phase 3. Safety, Immunogenicity, and Plans for Phase 3," AIDS Research and Human Retroviruses, vol. 14, Supplement 3, pp. S325-S331 (1998).
Gorny, M. K., et al., "Functional and Immunochemical Cross-Reactivity of V2-Specific Monoclonal Antibodies from HIV-1-Infected Individuals," Virology, vol. 427, No. 2, pp. 198-207, Author Manuscript—26 pages (Jun. 5, 2012).
Gorny, M. K., et al., "Human Anti-V2 Monoclonal Antibody That Neutralizes Primary but Not Laboratory Isolates of Human Immunodeficiency Virus Type 1," Journal of Virology, vol. 68, No. 12, pp. 8312-8320, (Dec. 1994).
Gorny, M. K., et al., "Identification of a New Quaternary Neutralizing Epitope on Human Immunodeficiency Virus Type 1 Virus Particles," Journal of Virology, vol. 79, No. 8, pp. 5232-5237, (Apr. 2005).
Harris, A., et al., "Trimeric HIV-1 Glycoprotein gp140 Immunogens and Native HIV-1 Envelope Glycoproteins Display the Same Closed and Open Quaternary Molecular Architectures," Proceedings of the National Academy of Sciences, vol. 108, No. 28, pp. 11440-11445, (Jul. 12, 2011).
Haynes, B. F., "Case control study of the RV144 trial for immune correlates: the analysis and way forward" presented at Plenary Session 01 Novel Approaches in Clinical Evaluation through Global Collaboration at the AIDS Vaccine Conference 2011, Bangkok, Thailand, 9 pages, (<http://www.aidsvaxwebcasts.org>) (Sep. 12-15, 2011).
Haynes, B.F., et al., "Aiming to induce broadly reactive neutralizing antibody responses with HIV-1 vaccine candidates", Expert Review of Vaccines, 2006, vol. 5, No. 3, pp. 347-363 (Author Manuscript—27 total pages).
Honnen, W. J., et al., "Type-Specific Epitopes Targeted by Monoclonal Antibodies with Exceptionally Potent Neutralizing Activities for Selected Strains of Human Immunodeficiency Virus Type 1 Map to a Common Region of the V2 Domain of gp120 and Differ Only at Single Positions from the Glade B Consensus Sequence," Journal of Virology, vol. 81, No. 3, pp. 1424-1432 (Feb. 2007).
International Preliminary Report on Patentability for PCT/US2012/045530 dated Jan. 16, 2014 consisting of 8 pages.
International Search Report for PCT/US2012/045530 dated Jan. 30, 2013 consisting of 4 pages.
Jeffs, S. A., et al: "Antigenicity of truncated forms of the human immunodeficiency virus type 1 envelope glycoprotein," Journal of General Virology, vol. 77, pp. 1403-1410 (1996).
Kasturi, S. P., et al, "Programming the Magnitude and Persistence of Antibody Responses with Innate Immunity," Nature, vol. 470, No. 7335, pp. 543-547, Author Manuscript—20 page (Feb. 24, 2011).
Kayman, S. C., et al., "Presentation of Native Epitopes in the V1/V2 and V3 Regions of Human Immunodeficiency Virus Type 1 gp120 by Fusion Glycoproteins Containing Isolated gp120 Domains," Journal of Virology, vol. 68, No. 1, pp. 400-410, (Jan. 1994).
Keele, B. F., et al., "Identification and Characterization of Transmitted and Early Founder Virus Envelopes in Primary HIV-1 Infection," Proceedings of the National Academy of Sciences, vol. 105, No. 21, pp. 7552-7557 (May 27, 2008).

Kwong, P. D., et al., "HIV-1 evades antibody-mediated neutralization through conformational masking of receptor-binding sites," Nature, vol. 420, pp. 678-682 (Dec. 12, 2002).
Lasky, L. A., et al., "Neutralization of the AIDS Retrovirus by Antibodies to a Recombinant Envelope Glycoprotein," Science, vol. 233, No. 4760, pp. 209-212, 5 pages (Jul. 11, 1986).
Liao H.-X., et al., "A Group M Consensus Envelope Glycoprotein Induces Antibodies That Neutralize subsets of Subtype B and C HIV-1 Primary Viruses," Virology, vol. 353, pp. 268-282 (2006).
Liao, H. X., et al., "High-throughput Isolation of Immunoglobulin Genes from Single Human B Cells and Expression as Monoclonal Antibodies," Journal of Virology Methods, vol. 158, Nos. 1-2, pp. 171-179, Author Manuscript—22 pages (Jun. 2009).
Liu, J., et al., "Molecular Architecture of Native HIV-1 gp120 Trimers," Nature, vol. 455, No. 7209, pp. 109-113, Author Manuscript—12 pages (Sep. 4, 2008).
Liu, P., et al., "Dynamic Antibody Specificities and Virion Concentrations in Circulating Immune Complexes in Acute to Chronic HIV-1 Infection," Journal of Virology, vol. 85, No. 21, pp. 11196-11207 (Nov. 2011).
McCutchan, F. E., et al., "Genetic Variants of HIV-1 in Thailand," AIDS Research and Human Retroviruses, vol. 8, No. 11, pp. 1887-1895, 18 pages (1992).
McLellan, J. S., et al., "Structure of HIV-1 gp120 V1/V2 Domain with Broadly Neutralizing Antibody PG9," Nature, vol. 480, No. 7377, pp. 336-343, Author Manuscript—17 pages (Dec. 15, 2012).
Pinter, A., et al., "Potent neutralization of primary HIV-1 isolates by antibodies directed against epitopes present in the V1/V2 domain of HIV-1 gp120," Vaccine, vol. 16, No. 19, pp. 1803-1811 (1998).
Pinter, A., et al., "The V1/V2 Domain of gp120 is a Global Regulator of the Sensitivity of Primary Human Immunodeficiency Virus Type 1 Isolates to Neutralization by Antibodies Commonly Induced upon Infection," Journal of Virology, vol. 78, No. 10, pp. 5205-5215 (May 2004).
Pitisuttithum, P., "HIV vaccine research in Thailand: lessons learned," Expert Rev. Vaccines, vol. 7, No. 3, pp. 311-317 (2008).
Rerks-Ngarm, S., et al., "Vaccination with ALVAC and AIDSVAX to Prevent HIV-1 Infection in Thailand," The New England Journal of Medicine, vol. 361, No. 23, pp. 2209-2220 (Dec. 3, 2009).
Safsten, P., et al., "Screening Antibody-Antigen Interactions in Parallel Using Biacore A100," Anal. Biochem., vol. 353, pp. 181-190 (2006).
Santra, S., et al., "Mosaic Vaccines Elicit CD8+ T Lymphocyte Responses in Monkeys that Confer Enhanced Immune Coverage of Diverse HIV Strains," Nature Med., vol. 16, No. 3, pp. 324-328, Author Manuscript—13 pages (Mar. 2010).
Shields, R. L., et al., "High Resolution Mapping of the Binding Site on Human IgG1 for $Fc_\gamma RI$, $Fc_\gamma RII$, $Fc_\gamma RIII$, and FcRn and Design of IgG1 Variants with Improved Binding to the $Fc_\gamma R$," Journal of Biological Chemistry, vol. 276, pp. 6591-6604, 27 pages (Nov. 28, 2000).
Smith, T. F. and Waterman, M. S., "Identification of Common Molecular Subsequences," Journal of Molecular Biology, vol. 147, pp. 195-197 (1981).
Torrieri-Dramard, L., et al., "Intranasal DNA Vaccination Induces Potent Mucosal and Systemic Immune Responses and Cross-protective Immunity Against Influenza Viruses," Molecular Therapy, vol. 19, No. 3, pp. 602-611 (Mar. 2011).
Tsao, C., et al., "Antigenicity and immunogenicity of transmitted/founder HIV envelope oligomers compared to chronic HIV envelopes", AIDS Research and Human Retroviruses, vol. 26, No. 10, Abstracts from AIDS Vaccine Conference 2010, Atlanta, Georgia, p. A-26, 2 pages (Sep. 28-Oct. 1, 2010).
Vancott, T. C., et al., "Dissociation rate of antibody-gp120 binding interactions is predictive of V3-mediated neutralization of HIV-1," J. Immunol., vol. 153, pp. 449-459, 12 pages (1994).
Written Opinion for PCT/US2012/045530 dated Jan. 30, 2013 consisting of 5 pages.
Yu, J.-S., et al., "Generation of Mucosal Anti-Human Immunodeficiency Virus Type 1 T-Cell Responses by Recombinant *Mycobacterium smegmatis*," Clinical and Vaccine Immunology, vol. 13, No. 11, pp. 1204-1211 (Nov. 2006).

(56) References Cited

OTHER PUBLICATIONS

Yu, J. S., et al., "Recombinant *Mycobacterium bovis* Bacillus Calmette-Guerin Elicits Human Immunodeficiency Virus Type 1 Envelope-Specific T Lymphocytes at Mucosal Sites," Clinical and Vaccine Immunol., vol. 14, No. 7, pp. 886-893 (Jul. 2007).

Zhu, P., et al., "Distribution and Three-Dimensional Structure of AIDS Virus Envelope Spikes," Nature, vol. 441: pp. 847-852, (Jun. 15, 2006).

Zolla-Pazner, S., et al., "V2-Reactive Antibodies in RV144 Vaccinees' Plasma", AIDS Research and Human Retroviruses, vol. 27, No. 10, Abstracts from AIDS Vaccine 2011, Bangkok, Thailand, p. A-21, 3 pages (Sep. 12-15, 2011).

Coico, R., et al., "The Genetic Basis of Antibody Structure," Immunology—A Short Course, Fifth Edition, Chapter 6, pp. 79-89, 13 total pages (2003), John Wiley & Sons, Inc., Hoboken, New Jersey.

* cited by examiner

Clonal lineage of V2,V3 conformational antibodies, CH01-CH04, their inferred intermediate antibodies (IAs, labeled 1, 2, and 3), and the inferred unmutated ancestor antibody (UA). Design of immunogens to drive such a pathway might involve producing the UA and IAs and using structure-based alterations in the antigen (i.e., changes in gp120 or gp140 predicted to enhance binding to UA or IA) or deriving altered antigens by a suitably designed selection strategy. Vaccine administration might prime with the antigen that binds UA most tightly, followed by sequential boosts with antigens optimized for binding to each IA. For this clonal lineage, an Env known to bind the UA (AE.A244 gp120: ref 21) could be a starting point for further immunogen design.
MRVKGIRKNCQQHLWRWGTMLLGILMICSAVPVWKEATTTLFCASDAKAYDTEVHNVWATHACVPTDPNPQE
MVLENVTEYFNMWKNNMVEQMHEDIISLWDQSLKPCVKLTPLCVTLTCTDYEWNCTGIRNSICKYNNMTNNS
SSGNYTGWERGEIKNCSFNSTISGIRDKVRKEYALLYKIDLVSIDGSNTSYRMISCNTSVITQSCPKISFEP
IPLHYCTPAGFALLKCNDKKFNGTGLCHNVSTVQCTHGIKPVVSTQLLLNGSLAEEEVVIRSKNFTDNAKII
IVQLNETVEINCTRPGNNTRKSIHIAPGRTFYATGEIIGDIRRAHCNISREKWNTTLHRIATKLREQYNKTI
VFNQSSGGDPEIVMHSVNCGGEFFYCNTSKLFNSTWNSTGGSISEDSENITLPCRIKQIVNMWQEVGKAMYA
PPIRGQIRCSSNITGLLLTRDGGINQSISETFRPGGGDMRDNWRSELYKYKVVKIEPLGIAPTKARERVVQR
EKE

FIGURE 9

SEQUENCE LISTING

```
<160> NUMBER OF SEQ ID NOS: 5

<210> SEQ ID NO 1
<211> LENGTH: 6
<212> TYPE: PRT
<213> ORGANISM: Human immunodeficiency virus

<400> SEQUENCE: 1

Glu Leu Asp Lys Trp Ala
1               5

<210> SEQ ID NO 2
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Arg Val Lys Glu Thr Gln Met Asn Trp Pro Asn Leu Trp Lys Trp
1               5                   10                  15

Gly Thr Leu Ile Leu Gly Leu Val Ile Ile Cys Ser Ala Ser Asp Asn
                20                  25                  30

Leu Trp Val Thr Val Tyr Tyr Gly Val Pro Val Trp Lys Glu Ala Asp
            35                  40                  45

Thr Thr Leu Phe Cys Ala Ser Asp Ala Lys Ala His Glu Thr Glu Val
        50                  55                  60

His Asn Val Trp Ala Thr His Ala Cys Val Pro Thr Asp Pro Asn Pro
65                  70                  75                  80

Gln Glu Ile Asp Leu Glu Asn Val Thr Glu Asn Phe Asn Met Trp Lys
                85                  90                  95

Asn Asn Met Val Glu Gln Met Gln Glu Asp Val Ile Ser Leu Trp Asp
                100                 105                 110

Gln Ser Leu Lys Pro Cys Val Lys Leu Thr Pro Pro Cys Val Thr Leu
            115                 120                 125

His Cys Thr Asn Ala Asn Leu Thr Lys Ala Asn Leu Thr Asn Val Asn
        130                 135                 140

Asn Arg Thr Asn Val Ser Asn Ile Ile Gly Asn Ile Thr Asp Glu Val
145                 150                 155                 160

Arg Asn Cys Ser Phe Asn Met Thr Thr Glu Leu Arg Asp Lys Lys Gln
                165                 170                 175
```

-continued

```
Lys Val His Ala Leu Phe Tyr Lys Leu Asp Ile Val Pro Ile Glu Asp
                180                 185                 190

Asn Asn Asp Ser Ser Glu Tyr Arg Leu Ile Asn Cys Asn Thr Ser Val
            195                 200                 205

Ile Lys Gln Pro Cys Pro Lys Ile Ser Phe Asp Pro Ile Pro Ile His
        210                 215                 220

Tyr Cys Thr Pro Ala Gly Tyr Ala Ile Leu Lys Cys Asn Asp Lys Asn
225                 230                 235                 240

Phe Asn Gly Thr Gly Pro Cys Lys Asn Val Ser Ser Val Gln Cys Thr
                245                 250                 255

His Gly Ile Lys Pro Val Val Ser Thr Gln Leu Leu Leu Asn Gly Ser
            260                 265                 270

Leu Ala Glu Glu Glu Ile Ile Ile Arg Ser Glu Asn Leu Thr Asn Asn
        275                 280                 285

Ala Lys Thr Ile Ile Val His Leu Asn Lys Ser Val Val Ile Asn Cys
    290                 295                 300

Thr Arg Pro Ser Asn Asn Thr Arg Thr Ser Ile Thr Ile Gly Pro Gly
305                 310                 315                 320

Gln Val Phe Tyr Arg Thr Gly Asp Ile Ile Gly Asp Ile Arg Lys Ala
                325                 330                 335

Tyr Cys Glu Ile Asn Gly Thr Glu Trp Asn Lys Ala Leu Lys Gln Val
            340                 345                 350

Thr Glu Lys Leu Lys Glu His Phe Asn Asn Lys Pro Ile Ile Phe Gln
        355                 360                 365

Pro Pro Ser Gly Gly Asp Leu Glu Ile Thr Met His His Phe Asn Cys
    370                 375                 380

Arg Gly Glu Phe Phe Tyr Cys Asn Thr Thr Arg Leu Phe Asn Asn Thr
385                 390                 395                 400

Cys Ile Ala Asn Gly Thr Ile Glu Gly Cys Asn Gly Asn Ile Thr Leu
                405                 410                 415

Pro Cys Lys Ile Lys Gln Ile Ile Asn Met Trp Gln Gly Ala Gly Gln
        420                 425                 430

Ala Met Tyr Ala Pro Pro Ile Ser Gly Thr Ile Asn Cys Val Ser Asn
    435                 440                 445

Ile Thr Gly Ile Leu Leu Thr Arg Asp Gly Gly Ala Thr Asn Asn Thr
450                 455                 460

Asn Asn Glu Thr Phe Arg Pro Gly Gly Gly Asn Ile Lys Asp Asn Trp
465                 470                 475                 480

Arg Asn Glu Leu Tyr Lys Tyr Lys Val Val Gln Ile Glu Pro Leu Gly
                485                 490                 495

Val Ala Pro Thr Arg Ala Lys Arg Arg Val Val Glu Arg Glu Lys Arg
            500                 505                 510

<210> SEQ ID NO 3
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Arg Val Lys Glu Thr Gln Arg Ser Trp Pro Asn Leu Trp Lys Trp
1               5                   10                  15

Gly Thr Leu Ile Leu Gly Leu Val Ile Met Cys Asn Ala Val Pro Val
                20                  25                  30
```

```
Trp Arg Asp Ala Asp Thr Thr Leu Phe Cys Ala Ser Asp Ala Gln Ala
        35                  40                  45

His Val Thr Glu Val His Asn Ile Trp Ala Thr His Ala Cys Val Pro
    50                  55                  60

Thr Asp Pro Asn Pro Gln Glu Ile His Leu Glu Asn Val Thr Glu Asn
65                  70                  75                  80

Phe Asn Met Trp Lys Asn Asn Met Ala Glu Gln Met Gln Glu Asp Val
                85                  90                  95

Ile Ser Leu Trp Asp Gln Ser Leu Lys Pro Cys Val Lys Leu Thr Pro
            100                 105                 110

Leu Cys Val Thr Leu Lys Cys Thr Ala Asn Ile Thr Ile Thr Asn Ala
            115                 120                 125

Thr Thr Arg Thr Glu Asn Thr Thr Lys Glu Asn Leu Ile Gly Asn Ile
        130                 135                 140

Thr Asp Glu Leu Arg Asn Cys Ser Phe Asn Val Thr Thr Glu Leu Arg
145                 150                 155                 160

Asp Arg Gln Arg Lys Ala Tyr Ala Leu Phe Tyr Lys Leu Asp Ile Val
                165                 170                 175

Pro Ile Asn Asn Glu Ala Asn Ser Ser Glu Tyr Arg Leu Ile Asn Cys
            180                 185                 190

Asn Thr Ser Val Ile Lys Gln Ala Cys Pro Lys Val Ser Phe Asp Pro
        195                 200                 205

Ile Pro Ile His Tyr Cys Thr Pro Ala Gly Tyr Ala Ile Leu Lys Cys
210                 215                 220

Asn Asp Lys Asn Phe Asn Gly Thr Gly Pro Cys Lys Asn Val Ser Ser
225                 230                 235                 240

Val Gln Cys Thr His Gly Ile Lys Pro Val Val Ser Thr Gln Leu Leu
                245                 250                 255

Leu Asn Gly Ser Leu Ala Glu Asp Glu Ile Ile Ile Arg Ser Glu Asn
            260                 265                 270

Leu Thr Asp Asn Ser Lys Asn Ile Ile Val His Leu Asn Glu Ser Val
        275                 280                 285

Val Ile Asn Cys Thr Arg Pro Ser Asn Asn Thr Val Lys Ser Ile Arg
290                 295                 300

Ile Gly Pro Gly Gln Thr Phe Tyr Arg Thr Gly Asp Ile Ile Gly Asp
305                 310                 315                 320

Ile Arg Gln Ala Tyr Cys Asn Val Asn Gly Thr Lys Trp Tyr Glu Val
                325                 330                 335

Leu Arg Asn Val Thr Lys Lys Leu Lys Glu His Phe Asn Asn Lys Thr
            340                 345                 350

Ile Val Phe Gln Gln Pro Pro Gly Gly Asp Leu Glu Ile Thr Thr
        355                 360                 365

His His Phe Asn Cys Arg Gly Glu Phe Phe Tyr Cys Asn Thr Thr Glu
    370                 375                 380

Leu Phe Asn Asn Thr Cys Val Asn Glu Thr Ile Asn Asn Gly Thr Glu
385                 390                 395                 400

Gly Trp Cys Lys Gly Asp Ile Ile Leu Pro Cys Arg Ile Lys Gln Ile
                405                 410                 415

Ile Asn Leu Trp Gln Glu Val Gly Gln Ala Met Tyr Ala Pro Pro Val
            420                 425                 430

Ser Gly Gln Ile Arg Cys Ile Ser Asn Ile Thr Gly Ile Leu Thr
        435                 440                 445
```

-continued

```
Arg Asp Gly Gly Asn Gly Lys Asn Gly Thr Leu Asn Asn Glu Thr Phe
    450                 455                 460

Arg Pro Gly Gly Gly Asn Met Lys Asp Asn Trp Arg Ser Glu Leu Tyr
465                 470                 475                 480

Lys Tyr Lys Val Val Glu Ile Glu Pro Leu Gly Ile Ala Pro Ser Arg
                485                 490                 495

Ala Lys Glu Arg Val Val Glu Met Lys Arg Glu Lys Glu
            500                 505

<210> SEQ ID NO 4
<211> LENGTH: 690
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Arg Val Lys Gly Ile Arg Lys Asn Cys Gln Gln His Leu Trp Arg
1               5                   10                  15

Trp Gly Thr Met Leu Leu Gly Ile Leu Met Ile Cys Ser Ala Ala Glu
                20                  25                  30

Asn Leu Trp Val Thr Val Tyr Tyr Gly Val Pro Val Trp Lys Glu Ala
            35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Met Val Leu Glu Asn Val Thr Glu Tyr Phe Asn Met Trp
                85                  90                  95

Lys Asn Asn Met Val Glu Gln Met His Glu Asp Ile Ile Ser Leu Trp
            100                 105                 110

Asp Gln Ser Leu Lys Pro Cys Val Lys Leu Thr Pro Leu Cys Val Thr
        115                 120                 125

Leu Thr Cys Thr Asp Tyr Glu Trp Asn Cys Thr Gly Ile Arg Asn Ser
    130                 135                 140

Ile Cys Lys Tyr Asn Asn Met Thr Asn Ser Ser Ser Gly Asn Tyr
145                 150                 155                 160

Thr Gly Trp Glu Arg Gly Glu Ile Lys Asn Cys Ser Phe Asn Ser Thr
                165                 170                 175

Ile Ser Gly Ile Arg Asp Lys Val Arg Lys Glu Tyr Ala Leu Leu Tyr
            180                 185                 190

Lys Ile Asp Leu Val Ser Ile Asp Gly Ser Asn Thr Ser Tyr Arg Met
        195                 200                 205

Ile Ser Cys Asn Thr Ser Val Ile Thr Gln Ser Cys Pro Lys Ile Ser
    210                 215                 220

Phe Glu Pro Ile Pro Leu His Tyr Cys Thr Pro Ala Gly Phe Ala Leu
225                 230                 235                 240

Leu Lys Cys Asn Asp Lys Lys Phe Asn Gly Thr Gly Leu Cys His Asn
                245                 250                 255

Val Ser Thr Val Gln Cys Thr His Gly Ile Lys Pro Val Val Ser Thr
            260                 265                 270

Gln Leu Leu Leu Asn Gly Ser Leu Ala Glu Glu Val Val Ile Arg
        275                 280                 285

Ser Lys Asn Phe Thr Asp Asn Ala Lys Ile Ile Ile Val Gln Leu Asn
    290                 295                 300
```

```
Glu Thr Val Glu Ile Asn Cys Thr Arg Pro Gly Asn Asn Thr Arg Lys
305                 310                 315                 320

Ser Ile His Ile Ala Pro Gly Arg Thr Phe Tyr Ala Thr Gly Glu Ile
            325                 330                 335

Ile Gly Asp Ile Arg Arg Ala His Cys Asn Ile Ser Arg Glu Lys Trp
                340                 345                 350

Asn Thr Thr Leu His Arg Ile Ala Thr Lys Leu Arg Glu Gln Tyr Asn
            355                 360                 365

Lys Thr Ile Val Phe Asn Gln Ser Ser Gly Gly Asp Pro Glu Ile Val
370                 375                 380

Met His Ser Val Asn Cys Gly Gly Glu Phe Phe Tyr Cys Asn Thr Ser
385                 390                 395                 400

Lys Leu Phe Asn Ser Thr Trp Asn Ser Thr Gly Gly Ser Ile Ser Glu
            405                 410                 415

Asp Ser Glu Asn Ile Thr Leu Pro Cys Arg Ile Lys Gln Ile Val Asn
                420                 425                 430

Met Trp Gln Glu Val Gly Lys Ala Met Tyr Ala Pro Pro Ile Arg Gly
            435                 440                 445

Gln Ile Arg Cys Ser Ser Asn Ile Thr Gly Leu Leu Leu Thr Arg Asp
450                 455                 460

Gly Gly Ile Asn Gln Ser Ile Ser Glu Thr Phe Arg Pro Gly Gly Gly
465                 470                 475                 480

Asp Met Arg Asp Asn Trp Arg Ser Glu Leu Tyr Lys Tyr Lys Val Val
            485                 490                 495

Lys Ile Glu Pro Leu Gly Ile Ala Pro Thr Lys Ala Arg Glu Arg Val
                500                 505                 510

Val Gln Arg Glu Lys Glu Ala Val Gly Ile Gly Ala Val Phe Leu Gly
            515                 520                 525

Phe Leu Gly Ala Ala Gly Ser Thr Met Gly Ala Ala Ser Leu Thr Leu
530                 535                 540

Thr Val Gln Ala Arg Leu Leu Leu Ser Gly Ile Val Gln Gln Gln Asn
545                 550                 555                 560

Asn Leu Leu Arg Ala Ile Glu Ala Gln Gln His Met Leu Gln Leu Thr
            565                 570                 575

Val Trp Gly Ile Lys Gln Leu Gln Ala Arg Val Leu Ala Leu Glu Arg
                580                 585                 590

Tyr Leu Arg Asp Gln Gln Leu Met Gly Ile Trp Gly Cys Ser Gly Lys
            595                 600                 605

Leu Ile Cys Thr Thr Ala Val Pro Trp Asn Ala Ser Trp Ser Asn Lys
610                 615                 620

Ser Leu Asn Asp Ile Trp Asn Asn Met Thr Trp Met Gln Trp Glu Arg
625                 630                 635                 640

Glu Ile Asp Asn Tyr Thr Gly Leu Ile Tyr Ser Leu Leu Glu Glu Ser
            645                 650                 655

Gln Asn Gln Gln Glu Lys Asn Glu Gln Asp Leu Leu Ala Leu Asp Lys
                660                 665                 670

Trp Ala Asn Leu Trp Thr Trp Phe Asp Ile Ser Asn Trp Leu Trp Tyr
            675                 680                 685

Ile Lys
690

<210> SEQ ID NO 5
<211> LENGTH: 507
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Arg Val Lys Gly Ile Arg Lys Asn Cys Gln Gln His Leu Trp Arg
1               5                   10                  15

Trp Gly Thr Met Leu Leu Gly Ile Leu Met Ile Cys Ser Ala Val Pro
            20                  25                  30

Val Trp Lys Glu Ala Thr Thr Thr Leu Phe Cys Ala Ser Asp Ala Lys
        35                  40                  45

Ala Tyr Asp Thr Glu Val His Asn Val Trp Ala Thr His Ala Cys Val
50                  55                  60

Pro Thr Asp Pro Asn Pro Gln Glu Met Val Leu Glu Asn Val Thr Glu
65                  70                  75                  80

Tyr Phe Asn Met Trp Lys Asn Asn Met Val Glu Gln Met His Glu Asp
                85                  90                  95

Ile Ile Ser Leu Trp Asp Gln Ser Leu Lys Pro Cys Val Lys Leu Thr
            100                 105                 110

Pro Leu Cys Val Thr Leu Thr Cys Thr Asp Tyr Glu Trp Asn Cys Thr
        115                 120                 125

Gly Ile Arg Asn Ser Ile Cys Lys Tyr Asn Asn Met Thr Asn Asn Ser
130                 135                 140

Ser Ser Gly Asn Tyr Thr Gly Trp Glu Arg Gly Glu Ile Lys Asn Cys
145                 150                 155                 160

Ser Phe Asn Ser Thr Ile Ser Gly Ile Arg Asp Lys Val Arg Lys Glu
                165                 170                 175

Tyr Ala Leu Leu Tyr Lys Ile Asp Leu Val Ser Ile Asp Gly Ser Asn
            180                 185                 190

Thr Ser Tyr Arg Met Ile Ser Cys Asn Thr Ser Val Ile Thr Gln Ser
        195                 200                 205

Cys Pro Lys Ile Ser Phe Glu Pro Ile Pro Leu His Tyr Cys Thr Pro
210                 215                 220

Ala Gly Phe Ala Leu Leu Lys Cys Asn Asp Lys Lys Phe Asn Gly Thr
225                 230                 235                 240

Gly Leu Cys His Asn Val Ser Thr Val Gln Cys Thr His Gly Ile Lys
                245                 250                 255

Pro Val Val Ser Thr Gln Leu Leu Asn Gly Ser Leu Ala Glu Glu
            260                 265                 270

Glu Val Val Ile Arg Ser Lys Asn Phe Thr Asp Asn Ala Lys Ile Ile
        275                 280                 285

Ile Val Gln Leu Asn Glu Thr Val Glu Ile Asn Cys Thr Arg Pro Gly
290                 295                 300

Asn Asn Thr Arg Lys Ser Ile His Ile Ala Pro Gly Arg Thr Phe Tyr
305                 310                 315                 320

Ala Thr Gly Glu Ile Ile Gly Asp Ile Arg Arg Ala His Cys Asn Ile
                325                 330                 335

Ser Arg Glu Lys Trp Asn Thr Thr Leu His Arg Ile Ala Thr Lys Leu
            340                 345                 350

Arg Glu Gln Tyr Asn Lys Thr Ile Val Phe Asn Gln Ser Ser Gly Gly
        355                 360                 365

Asp Pro Glu Ile Val Met His Ser Val Asn Cys Gly Gly Glu Phe Phe
370                 375                 380

```
Tyr Cys Asn Thr Ser Lys Leu Phe Asn Ser Thr Trp Asn Ser Thr Gly
385                 390                 395                 400

Gly Ser Ile Ser Glu Asp Ser Glu Asn Ile Thr Leu Pro Cys Arg Ile
                405                 410                 415

Lys Gln Ile Val Asn Met Trp Gln Glu Val Gly Lys Ala Met Tyr Ala
            420                 425                 430

Pro Pro Ile Arg Gly Gln Ile Arg Cys Ser Ser Asn Ile Thr Gly Leu
            435                 440                 445

Leu Leu Thr Arg Asp Gly Gly Ile Asn Gln Ser Ile Ser Glu Thr Phe
        450                 455                 460

Arg Pro Gly Gly Gly Asp Met Arg Asp Asn Trp Arg Ser Glu Leu Tyr
465                 470                 475                 480

Lys Tyr Lys Val Val Lys Ile Glu Pro Leu Gly Ile Ala Pro Thr Lys
                485                 490                 495

Ala Arg Glu Arg Val Val Gln Arg Glu Lys Glu
                500                 505
```

GP120 IMMUNOGENS AND METHODS INDUCING NEUTRALIZING ANTIBODIES TO HUMAN IMMUNODEFICIENCY VIRUS

This application is a U.S. National Phase of International Application No. PCT/US2012/000442, filed Oct. 3, 2012, which designated the U.S. and claims priority from U.S. Provisional Application No. 61/542,469, filed Oct. 3, 2011 and U.S. Provisional Application No. 61/708,503, filed Oct. 1, 2012, the entire contents of each of which are incorporated herein by reference.

TECHNICAL FIELD

The present invention relates, in general, to an HIV-1 vaccine and, in particular, to a B cell lineage-based vaccination protocol.

BACKGROUND

The traditional strategies for vaccine development have been to make killed, attenuated or subunit preparations as homologous prime/boosts, and then to test them for safety and efficacy[1,2]. Vaccines developed in this way are used world-wide for both bacterial and viral infectious diseases[1-4]. A number of viral targets have so far resisted this classical vaccine-development scheme—HIV-1, dengue and hepatitis C among them[5-7]. Broadly protective influenza vaccines have also yet to be been achieved[8]. HIV-1 is thus a paradigm of those viral diseases for which inducing broadly neutralizing antibodies is especially difficult[9,10].

For many of the viral vaccines in current use, induction of neutralizing antibodies is a principal correlate of protection[3,4]. Efforts to find new vaccine-development strategies have therefore focused on design of immunogens bearing epitopes with high affinity for plasma antibodies produced by memory B cells. This strategy assumes that the antigens recognized by memory B cells in a vaccine boost are the same as those recognized by naïve B cells during the priming immunization. For both HIV-1 and influenza, however, this strategy has not, as yet, led to induction in a majority of vaccines of antibodies that neutralize a satisfactorily wide range of virus strains. The failure may stem in part from characteristics of the chosen immunogens (e.g., glycan masking of HIV-1 envelope protein epitopes[9]: Table 1) and in part from limited accessibility of conserved epitopes on the viral antigen[8] (e.g., the "stem" and sialic-acid binding epitopes on influenza HA). Mimicry of host antigens by some of these conserved epitopes may be another complication, leading to suppression of a potentially useful antibody response[11].

TABLE 1

Factors preventing induction of long-lasting broad neutralizing HIV-1 antibodies Neutralizing epitopes masked by carbohydrates
Conformational flexibility of HIV-1 envelope
Transient neutralizing epitope expression
Molecular mimicry of Env carbohydrates and protein regions of host molecules
Tolerance control of gp41 neutralizing epitope responses
Half-life of all induced antibodies to Env are short; failure of Env to induce long-lived plasma cells
Rapid viral escape from induced neutralizing antibodies

TABLE 1-continued

Factors preventing induction of long-lasting broad neutralizing HIV-1 antibodies Diversion of B cell responses from neutralizing determinants by immune dominant, non-neutralizing epitopes of Env
Requirement for extensive somatic hypermutations, and requirement for complex maturation pathways Making vaccines for infectious agents with transient, cryptic or host-mimicking epitopes may require detailed understanding of antibody affinity maturation—in particular, of patterns of maturation that lead to rare, broadly protective antibodies[12-14]. It might then be possible to design immunogens that increase the likelihood of maturation along those pathways. Recent data from animal studies have demonstrated that the B cells that survive and persist in the germinal center reaction are those presenting B-cell receptors with the highest affinity for antigen[15-18]. Moreover, for some responses to viral antigens, the antigen that stimulates memory B cells during affinity maturation and the antigen that initially elicits naïve B cells may not be the same[12-14, 19-21]. Thus, to induce the processes that lead to such a protective response, it may be necessary to use one antigen for the vaccine prime (to trigger naïve B cells) and others in boosts that drive affinity maturation[12-14, 20-23].

Described herein is an approach to vaccine design based on insights from basic B cell biology, structural biology, and new methods for inferring unmutated ancestor antibodies as estimates of naïve B-cell receptors and their clonal lineage progeny. While the focus is on the biology of inducing broadly neutralizing antibodies to the HIV-1 Env, parallels are also drawn to issues for influenza vaccine development.

Biology of B Cells and Antibody Responses.

Human B cells arise from committed progenitors that express the V(D)J recombinase, RAG1 and RAG2, to effect genomic rearrangements of the IGH gene loci[24-27]. In pre-B I cells, functional μH polypeptides formed by these rearrangements associate with surrogate light chains (SLC)[28-30] and Igα/Igβ heterodimers to form pre-B cell receptors (pre-BCR)[31] necessary for cell survival and proliferation[24, 32, 33]. These cells exit the cell cycle[25] as pre-B II cells, initiate rearrangements in the κ- or λ light (L)-chain loci[34, 35], and assemble a mature BCR[36, 37] that binds antigen[24, 38] (FIG. 1). The generation of a BCR by genomic rearrangement and the combinatorial association of IG V, D, and J gene segments ensures a diverse primary repertoire of BCR and antibodies but also produces self-reactive cells with significant frequency[39].

Most immature B cells are autoreactive; they are consequently eliminated or inactivated by immunological tolerance[40, 41]. The remaining B cells mature through the transitional 1 (T1) and T2 stages characterized by changes in membrane IgM (mIgM) density, mIgD expression, and the loss/diminution of CD10 and CD38[42]. In the periphery, newly formed (T2) B cells are subject to a second round of immune tolerization before entering the mature B cell pools[40, 41]. Each of these stages in B-cell development is defined by a characteristic genomic and physiologic status (FIG. 1); in concert, these events specify the potential of humoral immunity.

At least three mechanisms of immunological tolerance deplete the immature and maturing B-cell pools of self-reactivity: apoptotic deletion[43, 44], cellular inactivation by anergy[45, 46], and the replacement of autoreactive BCR by secondary V(D)J rearrangements[39, 47-49]. The great majority of lymphocytes that commit to the B-cell lineage do not reach the immature B cell stage because they express dysfunctional µH polypeptides and cannot form a pre-BCR[50, 51] or because they carry self-reactive BCR[40].

Autoreactive BCR frequencies decline with increasing developmental maturity[43, 47], even for cells drawn from peripheral sites [FIG. 1][52, 53]. The final stages of B-cell development and tolerization occur in secondary lymphoid tissues where newly formed (T2) B cells undergo selection into mature B-cell compartments[54, 55]. Tolerance mechanisms, especially apoptotic deletion[54-56], operate during the transitional stages of B-cell development, and the frequency of self-reactive cells decreases substantially after entry into the mature pools[40]. The effects of these tolerizing processes have been followed directly in humans by recovering and expressing IgH and IgL gene rearrangements from individual immature, transitional, or mature B cells and determining the frequencies at which the reconstituted Abs react with human cell antigens[40, 47].

Despite the multiple tolerance pathways and checkpoints, not all autoreactive B cells are removed during development[41]. In mice, mature follicular B cells are substantially purged of autoreactivity, but the marginal zone (MZ) and B1 B cell compartments are enriched for self-reactive cells[57]. In humans, some 20%-25% of mature, naïve B cells circulating in the blood continue to express autoreactive BCR[35, 40, 41].

Not all selection during B-cell development is negative. Careful accounting of $V_H$ gene segment usage in immature and mature B-cell populations suggests that positive selection also occurs in the transitional stages of B-cell development[58, 59], but the mechanisms for such selection are obscure. The substantial selection imposed on the primary B-cell repertoire, negative and positive, by these physiologic events implies that the full potential of the primary, or germline, BCR repertoire is not available to vaccine immunogens. Only those subsets of naïve mature B cells that have been vetted by tolerance or remain following endogenous selection can respond. For microbial pathogens and vaccine antigens that mimic self-antigen determinants, the pool of mature B cells capable of responding can, therefore, be quite small or absent altogether.

This censoring of the primary BCR repertoire by tolerance sets up a road block in the development of effective HIV-1 vaccines as the success of naïve B cells in humoral responses is largely determined by BCR affinity[15-17]. If immunological tolerance reduces the BCR affinity and the numbers of naïve B cells that recognize HIV-1 neutralizing epitopes, humoral responses to those determinants will be suppressed. Indeed, HIV-1 infection and experimental HIV-1 vaccines are very inefficient in selecting B cells that secrete high affinity, broadly neutralizing, HIV-1 antibodies[5, 60-62].

The predicted effects of immune tolerance on HIV-1 BnAb production has been vividly illustrated in 2F5 VDJ "knock-in" (2F5 VDJ-KI) mice that contain the human VDJ gene rearrangement of the 2F5 BnAb[61, 62]. In 2F5 VDJ-KI mice, early B-cell development is normal, but the generation of immature B cells is severely impaired in a manner diagnostic of tolerization of auto-reactive BCR[43, 44]. Subsequent studies show that the 2F5 mAb avidly binds both mouse and human kynureninase, an enzyme of tryptophan metabolism, at an α-helical motif that matches exactly the 2F5 MPER epitope: ELDKWA[63] (SEQ ID NO: 1) (Yang, G., Haynes, B. F., Kelsoe, G. et al., unpublished)

Despite removal of most autoreactive B cells by the central and peripheral tolerance checkpoints[40, 41], antigen-driven, somatic hypermutation in mature, germinal center (GC) B cells generate de novo self-reactivity, and these B cell mutants can become memory B cells[64-66]. Thus, Ig hypermutation and selection in GC B cells not only drive affinity maturation[15, 18, 67-69], but also create newly autoreactive B cells that appear to be controlled only weakly[43, 70-72] by immunoregulation. At least two factors limit this de novo autoreactivity: the availability of T-cell help[18, 73] and the restricted capacity of GC B cells to accumulate serial mutations that do not compromise antigen binding and competition for cell activation and survival[18, 67, 74].

Eventually, V(D)J hypermutation approaches a ceiling, at which further mutation can only lower BCR affinity and decrease cell fitness[73-75]. The mean frequency of human Ig mutations in secondary immune responses is roughly 5%[20, 76, 77], and the significantly higher frequencies (10%-15%) of mutations in Ig rearrangements that encode HIV-1 BnAbs[5, 11] therefore suggest atypical pathways of clonal evolution and/or selection. In contrast to clonal debilitation by high mutational burden[73-75], HIV-1 BnAbs appear to require extraordinary frequencies of V(D)J misincorporation[5, 11]. Perhaps the most plausible explanation for this unusual characteristic is serial induction of Ig hypermutation and selection by distinct antigens. This explanation also suggests pathways for generating antibody responses that are normally proscribed by the effects of tolerance on the primary BCR repertoire.

In GC, clonally related B cells rapidly divide; their clonal evolution is a Darwinian process comprising two component sub-processes: Ig hypermutation and affinity-dependent selection[18, 67, 78]. Selection is nonrandom of course, but even hypermutation is non-random, influenced substantially by local sequence context[79] due to the sequence specificity of activation-induced cytidine deaminase (AICDA)[80]. Furthermore, the codon bias exhibited by Ig genes increases the likelihood of mutations in the regions that encode the antigen-binding domains[81]. Even prior to selection, therefore, some evolutionary trajectories are favored over others. Continued survival and proliferation of GC B cells is strongly correlated with BCR affinity and appears to be determined by each B cell's capacity to collect and present antigen[18, 67] to local CXCR5$^+$CD4$^+$ T (T$_{FH}$) cells[82].

Unlike AICDA-driven hypermutation, where molecular biases remain constant, clonal selection in GC is relative to antibody fitness (affinity and specificity) and changes during the course affinity maturation. Individual GC, therefore, represent microcosms of Darwinian selection, and each is essentially an independent "experiment" in clonal evolution that is unique with regard to the founding B and T cell populations and the order and distribution of introduced mutations.

The poor efficiency with which either infection or immunization elicits BnAbs and the unusually high frequency of Ig mutations present in most BnAb gene rearrangements imply that BnAb B cells are products of disfavored and tortuous pathways of clonal evolution. Because BCR affinity is the critical determinant of GC B cell fitness, it should be possible to select a series of immunogens that direct GC B-cell evolution along normally disfavored pathways. Any method for directed somatic evolution must take into account the complex and interrelated processes of Ig hypermutation, affinity-driven selection, and cognate interaction with T$_{FH}$. These hurdles are not insignificant, but neither are they necessarily insurmountable. Indeed, BnAb responses elicited by HIV-1 infection may represent an example of fortuitous sequential immunizations that, by chance, favor the development of BnAb B cells from unreactive, naïve populations.

Biology of Antibody Responses to HIV-1 as a Paradigm of Difficult-to-Induce Broadly Neutralizing Antibodies The initial antibody response to HIV-1 following transmission is to non-neutralizing epitopes on gp41[20, 83]. This initial Env antibody response has no anti-HIV-1 effect, as indicated by its failure to select for virus escape mutants[83]. The first antibody response that can neutralize the transmitted/founder virus in vitro is to gp120, is of extremely limited breadth, and appears only ~12-16 weeks after transmission[84, 85].

Antibodies to HIV-1 envelope that neutralize a broad range of HIV-1 isolates have yet to be induced by vaccination and appear in only a minority of subjects with chronic HIV-1 infection[5] (FIG. 2). Indeed, only ~20% of chronically infected subjects eventually make high levels of broadly neutralizing antibodies, and then not until after ~4 or more years of infection[86]. Moreover, when made, broadly neutralizing antibodies are of no clinical benefit, probably because they have no effect on the well-established, latent pool of infected CD4 T cells[86].

Goals for an HIV-1 Vaccine

Passive infusion of broadly neutralizing human monoclonal antibodies (mAbs) can protect against subsequent challenge with simian-human immunodeficiency viruses (SHIVs) at antibody levels thought to be achievable by immunization[87-90]. Thus, despite the obstacles, a major goal of HIV-1 vaccine development is to find strategies for inducing antibodies with sufficient breadth to be practically useful at multiple global sites.

Recent advances in isolating human mAbs using single cell sorting of plasmablasts/plasma cells[20,76] or of antigen-specific memory B cells decorated with fluorescently labeled antigen protein[91, 92], and clonal cultures of memory B cells that yield sufficient antibody for high throughput functional screening[22, 93, 94], have led to isolation of mAbs that recognize new targets for HIV-1 vaccine development (FIG. 2). Those broadly neutralizing antibodies that are made in the setting of chronic HIV-1 infection have one or more of the following unusual traits: restricted heavy-chain variable region ($V_H$) usage, long HCDR3s, a high level of somatic mutations, and/or antibody polyreactivity for self or other non-HIV-1 antigens (rev. in[5, 11]). Some of these HIV BnAbs have been reverted to their unmutated ancestral state and found to bind poorly to native HIV-1 Env[12, 14]. This observation has suggested the notion of different or non-native immunogens for priming the Env response followed by other immunogens for boosting[12-14, 20-23]. Thus, the B cell lineage design strategy described herein is an effort to drive rare or complex B cell maturation pathways.

SUMMARY OF THE INVENTION

The present invention relates, in general; to an HIV-1 vaccine and, in particular, to a B cell lineage immunogen design.

Objects and advantages of the present invention will be clear from the description that follows.

BRIEF DESCRIPTION OF THE DRAWINGS

FIG. 3. Clonal lineage of V2,V3 conformational antibodies, CH01-CH04, their inferred intermediate antibodies (IAs, labeled 1, 2, and 3), and the inferred unmutated ancestor antibody (UA). Design of immunogens to drive such a pathway might involve producing the UA and IAs and using structure-based alterations in the antigen (i.e., changes in gp120 or gp140 predicted to enhance binding to UA or IA) or deriving altered antigens by a suitably designed selection strategy. Vaccine administration might prime with the antigen that binds UA most tightly, followed by sequential boosts with antigens optimized for binding to each IA. For this clonal lineage, an Env known to bind the UA (AE.A244 gp120: ref 21) could be a starting point for further immunogen design.

Figure 8:
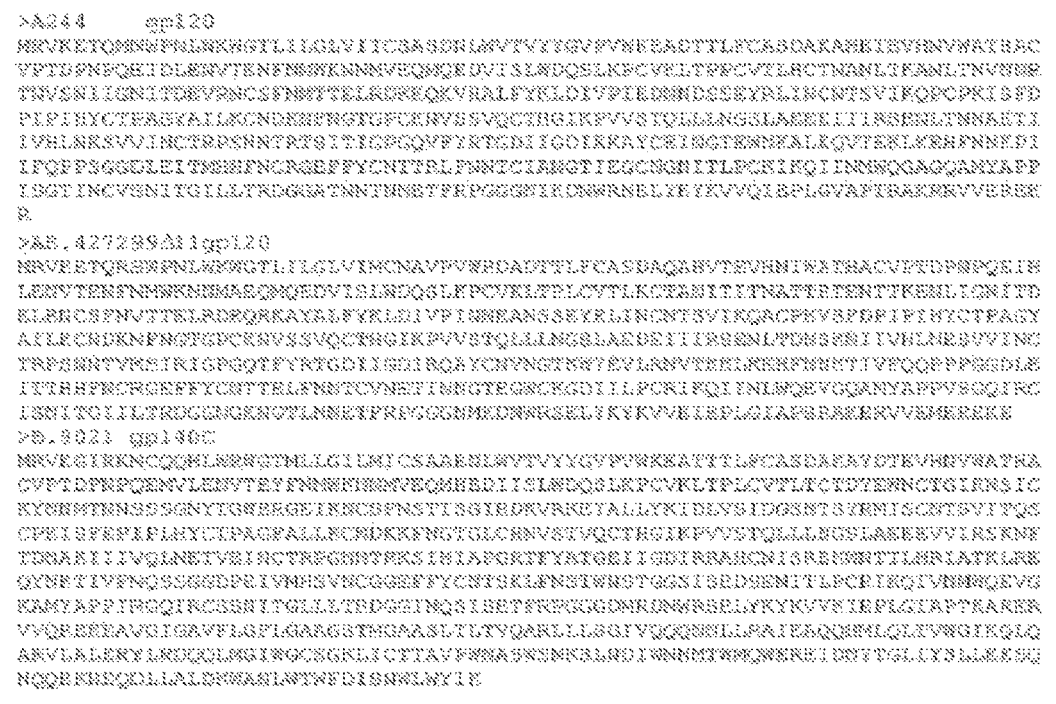

FIG. 8. Sequences of A244 gp120 (SEQ ID NO: 2), AE. 427299Δ11gp120 (SEQ ID NO: 3), and B.9021 gp140C (SEQ ID NO: 4).

FIG. 9. Sequence of 9021 Δ11 gp120 (SEQ ID NO: 5).

DETAILED DESCRIPTION OF THE INVENTION

Definitions of Terms

Figure 1:
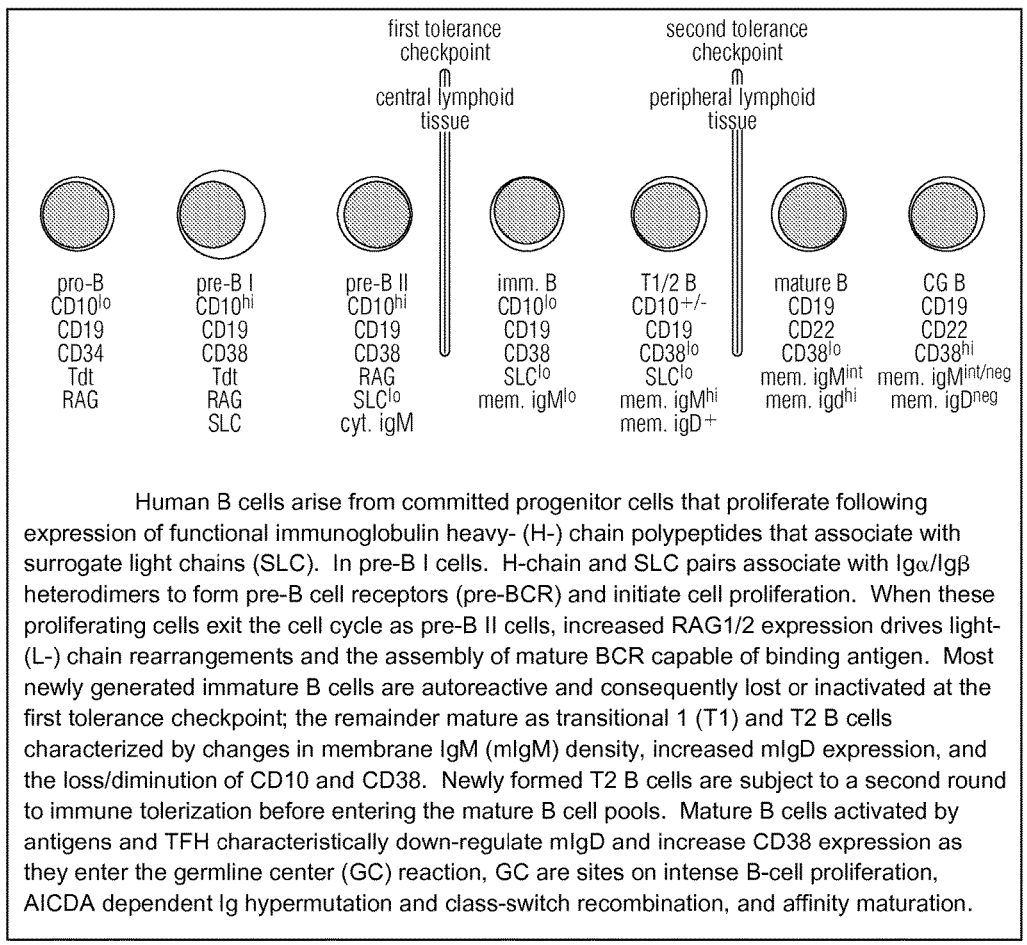
FIG. 1. Human B cells arise from committed progenitor cells that proliferate following expression of functional immunoglobulin heavy- (H-) chain polypeptides that associate with surrogate light chains (SLC). In pre-B I cells. H-chain and SLC pairs associate with Igα/Igβ heterodimers to form pre-B cell receptors (pre-BCR) and initiate cell proliferation. When these proliferating cells exit the cell cycle as pre-B II cells, increased RAG1/2 expression drives light- (L-) chain rearrangements and the assembly of mature BCR capable of binding antigen. Most newly generated immature B cells are autoreactive and consequently lost or inactivated at the first tolerance checkpoint; the remainder mature as transitional 1 (T1) and T2 B cells characterized by changes in membrane IgM (mIgM) density, increased mIgD expression, and the loss/diminution of CD10 and CD38. Newly formed T2 B cells are subject to a second round to immune tolerization before entering the mature B cell pools. Mature B cells activated by antigens and TFH characteristically down-regulate mIgD and increase CD38 expression as they enter the germline center (GC) reaction, GC are sites on intense B-cell proliferation, AICDA dependent Ig hypermutation and class-switch recombination, and affinity maturation.

Autologous neutralizing antibodies: Antibodies that are produced first after transmission of HIV-1 and that selectively neutralize the transmitted/founder virus.

B-cell anergy: A type of B cell tolerance that renders potentially responding B cells unresponsive to antigen.

B-cell tolerance: The activity of the immune system to suppress B cells that are dangerously host reactive. These cells are either deleted from the B cell repertoire or rendered unresponsive or anergic. A third tolerance mechanism is swapping of either light chains (light chain editing) or heavy chains (heavy chain editing) to prevent self-reactivity of antibodies.

Broadly neutralizing antibodies (BnAbs): Antibodies produced by B cells that neutralize diverse strains of a particular infectious agent.

CD4-binding-site gp120 broadly neutralizing antibodies: The T-lymphocyte surface antigen, CD4, is the cellular receptor of HIV-1. It binds at a defined, conserved site on gp 120. Although many antibodies recognize the region on the surface gp120 that includes the CD4 binding site, their footprint also covers adjacent parts of the surface, where mutation can lead to escape from neutralization by those antibodies. A few, broadly neutralizing antibodies (the VRC01-VRC03 clonal lineage, PG04, the CH30-CH34 clonal lineage) bind gp120 in a way that closely resembles the contact made by CD4: the heavy-chain VH region of these antibodies (nearly all are $V_H$ 1~2) mimics the N-terminal, Ig-like domain of CD4, with relatively few interactions outside the conserved, CD4-binding pocket.

Germinal center: Location in immune tissues at which dendritic and other cells present B cell contact antigen, helper T cells make contact with B cells, and immunoglobulin class switching and somatic hypermutation take place.

Heavy chain third complementary determining region (HCDR3): Three loops from each of the two immunoglobulin polypeptide chains contribute to its antigen-binding surface. The third of these "complementarity determining regions" (CDRs) on the heavy chain is particularly variable and often makes a particularly important contribution to antigen recognition.

Hemagglutinin broadly neutralizing determinants: The influenza virus hemagglutinin (HA), one of the two principal surface proteins on influenza A and B, has, like HIV-1 Env, both strain-specific and conserved determinants for neutralizing antibodies. Like HIV-1 Env neutralizing antibodies, most hemagglutinin neutralizing antibodies are strain specific and not broadly neutralizing. The conserved targets of broadly neutralizing influenza antibodies are the binding pocket for the receptor, sialic acid, and the "stalk" of the rod-like HA trimer.

Immunoglobulin class switching: The process in germinal centers by which antigen drives switching of immunoglobulin made by a developing memory B cell from IgM to IgG, IgA or IgE. This process, which requires activation of the recombination activating genes I and II (RAGI, RAGII), is independent of somatic hypermutation. Not all memory B cells undergo class switching, however, and some memory B cells retain surface IgM.

Intermediate antibodies (IAs): Antibodies made by intermediates in the clonal lineage generated by affinity maturation of a naïve B cell in a germinal center.

Membrane-proximal-external-region (MPER) gp41 broadly neutralizing antibodies: The MPER is a site on HIV-1 Env gp41 near the viral membrane at which a number of neutralizing antibodies bind. Isolated natural antibodies that bind this region (2F5, 4E10, CAP206-CH12) are polyreactive; the tip of their HCDR3 associates with the viral lipid membrane while awaiting exposure of the gp41 intermediate neutralizing determinant.

Polyreactivity: the common characteristic of those virus-specific antibodies that also bind either host self antigens or other non-viral antigens.

V2, V3 conformational (quaternary) HIV-1 envelope gp120 broadly neutralizing antibodies: A group of HIV-1 broadly neutralizing antibodies recognizing an epitope on gp120 that is properly configured only (or primarily) when gp120 is part of the complete Env trimer. Mutational analysis of regions of gp120 that bind quaternary antibodies show that most of them recognize the second variable (V2) and third variable (V3) loops of HIV-1 Env. Examples include PG9, PG16 and the CH01-04 clonal lineage of human mAbs.

Somatic hypermutation: The process in germinal centers, mediated by the enzyme activation-induced cytidine deaminase (AID), that leads to affinity maturation of the antibody-antigen contact.

Third variable loop neutralizing antibodies: The third variable loop of HIV-1 envelope (V3) is part of the binding site for the CCR5 and CXCR4 Env co-receptors; it is a frequent target of neutralizing antibodies. Examples of V3 neutralizing antibodies isolated from chronically infected subject are 447, 19b and CH19. The V3 loops is masked on the envelopes of most transmitted/founder viruses, and thus V3 loop antibodies by themselves are likely to be of limited value as a vaccine response. V3 loop antibodies are easily elicited, however, and they could be useful in combination with an antibody that induced V3 loop exposure (e.g., a CD4-binding-site antibody).

Unmutated ancestor antibodies (UAs): Antibodies that represent the B cell receptors (BCRs) on naïve B cells. UAs can be isolated from naïve or transitional B cell populations or inferred from memory B-cell mutated clonal lineages.

VH restriction: occurrence of the same $V_H$ in the antibody responses of many different individuals to the same epitope.

B Cell Lineage Vaccine Design

FIG. 3 shows a general outline for B-cell lineage vaccine design. There are several points that distinguish this approach from previous vaccination strategies. First, existing vaccines generally use the same immunogens for prime as for boosts. In the scheme outlined in FIG. 3, different antigens can be used for multiple steps. Design of the priming antigen can utilize the B cell receptor from the inferred unmutated ancestor (UA, see below) or from an actual, isolated naïve B cell as a template, while design of boosting antigens can use the B-cell receptor from inferred (or isolated) maturation intermediates as templates (see immunogen design section below)[68]. Second, the B cell lineage notion targets, for the priming immunogen, the earliest stages of B cell clonal development, following the basic understanding of B cell antigen drive reviewed above (FIG. 1). Third, for boosting immunogens, the scheme in FIG. 3 anticipates choosing components that might have the highest affinity for early stages of B cell maturation.

Figure 2:
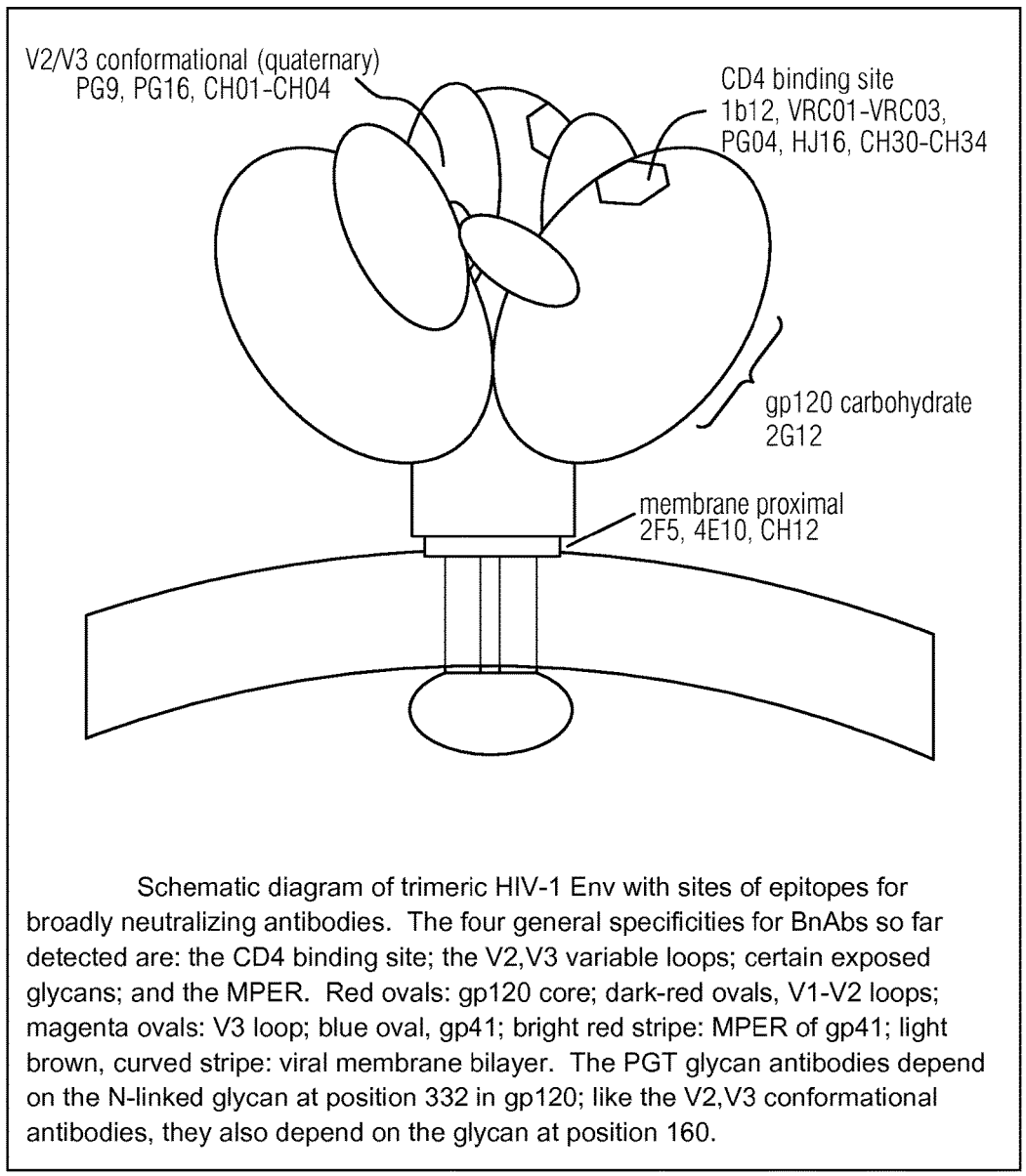
FIG. 2. Schematic diagram of trimeric HIV-1 Env with sites of epitopes for broadly neutralizing antibodies. The four general specificities for BnAbs so far detected are: the CD4 binding site; the V2,V3 variable loops; certain exposed glycans; and the MPER. Red ovals: gp120 core; dark-red ovals, V1-V2 loops; magenta ovals: V3 loop; blue oval, gp41; bright red stripe: MPER of gp41; light brown, curved stripe: viral membrane bilayer. The PGT glycan antibodies depend on the N-linked glycan at position 332 in gp120; like the V2,V3 conformational antibodies, they also depend on the glycan at position 160.

Three general steps are contemplated for any lineage-based approach to vaccine design. First, identify a set of clonally related memory B cells, using single cell technology to obtain the native variable heavy ($V_H$) and variable light ($V_L$) chain pairs. Second, infer with the computational methods described below, the unmutated ancestral B-cell receptor (i.e., the presumptive receptor of the naïve B cell to be targeted), along with likely intermediate antibodies (IAs) at each clonal lineage branch point (FIG. 2, circular nodes 1-3). Finally, design immunogens with enhanced affinity for UA and IAs, using the UA and IAs as structural templates (FIG. 3). Thus, in contrast to the usual vaccine immunogens that prime and boost with the same immunogen, a B cell lineage-based vaccination protocol can prime with one immunogen and boost with another, and potentially boost with a sequence of several different immunogens[12-14, 20-23] (FIG. 3). In recent work, a gp140 Env antigen that did not bind the UA of a BnAb was modified by native deglycosylation; unlike the untreated native Env antigen, the deglycosylated gp140 Env bound the BnAb UA with reasonable efficiency. Immunization of rhesus macaques showed that the Env that bound well to the UA was the superior immunogen[19].

It is important to note that variability of the antibody repertoire among individuals poses a potential problem for this strategy: a clonal lineage isolated from one subject may not be relevant for inducing a similar antibody in another subject. Recent observations of limited VH usage summarized above suggest that for some viral neutralizing epitopes the relevant immunoglobulin repertoire is restricted to a very small number of VH families and that the maturation pathways may be similar among individuals or require the same immunogens to drive similar pathways of affinity maturation. One example of convergent evolution of human antibodies in different individuals comes from work on B cell chronic lymphocytic leukemia (B cell CLL), in which similar B CLL VH HCDR3 sequences can be found in different people[95, 96]. A second comes analysis of influenza and HIV-1 VH1-69 antibodies, in which similar VH1-69 neutralizing antibodies can be isolated from different subjects[97-101]. A third example comes from structures of V2,V3 conformational (quaternary) antibodies in which the antibodies have very similar HCDR3 structures but arise from different VH families[22, 101, 102]. Recently, use of 454 deep sequencing technology has shown convergent evolution of VH1-2 and VH1-46 CD4 in maturation of broadly neutralizing antibodies, but determining how distinct the affinity maturation pathways are for each specificity of HIV-1 broadly neutralizing antibodies requires experimental testing. Nonetheless, for major classes of such antibodies, the data summarized suggest commonalties among affinity maturation pathways in different individuals.

Inferring UAs and Intermediates of BnAb Clonal Lineages

B cell lineage immunogen design requires that it be possible to infer from the sequences of the mature mutated antibodies in a lineage those of the intermediate and unmutated ancestors, as in the reconstructed clonal lineage in FIG. 2. Antibody genes are assembled from a fixed set of gene segments; that there are relatively small numbers (i.e., non-astronomical) of possible genes ancestral to any given set of clonally-related antibody genes allows one to infer the ancestor antibodies[20-23].

The starting point for any likelihood-based phylogenetic analysis is a model for the introduction of changes along the branches. For the inference of unmutated ancestor antibodies of a clonal lineage (See UA, FIG. 3), a model is needed for somatic mutation describing the probability that a given nucleotide (for example, the one at position 21 in the V region gene) that initially has state $n_1$ will, after the passage oft units of evolutionary time, have state $n_2$. This substitution model makes it possible to compute the probability of the observed data given any hypothesized ancestor. From there, the application of Bayes' rule provides the posterior probability for any hypothesized ancestor. The posterior probability at each position in the unmutated ancestor can now be computed from the posteriors over the gene segments and over other parameters of the rearrangement. The complete probability function provides a measure of the certainty of the inference at each position in addition to the most-likely nucleotide state itself. This additional information may be crucial to ensuring the relevance of subsequent assays performed on the synthesized unmutated ancestor. Some of the intermediate forms of the antibody genes through which a given member of the clone passed can be similarly inferred, though not all of them (antibodies at nodes 1-3, FIG. 3). The more members of the antibody clone that it is possible to isolate, the higher the resolution with which the clonal intermediates can be reconstructed[20]. 454 deep sequencing has recently proved useful for expanding the breadth and depth of clonal lineages[20, 23].

Using UAs and IAs as Templates for Immunogen Design

The goal of the immunogen-design strategy described herein is to derive proteins (or peptides) with enhanced affinity for the unmutated common ancestor of a lineage or for one or more of the inferred intermediate antibodies. The method of choice for finding such proteins will clearly depend on the extent of structural information available. In the most favorable circumstances, one might have crystal structures for the complex of the mature antibody (Fab) with antigen, structures of the UA and of one or more IAs, and perhaps a structure of an IA:antigen complex. It is likely that the native antigen will not bind tightly enough to the UA to enable structure determination for that complex. In the absence of any direct structural information, consideration can also be given to cases in which the antibody footprint has been mapped by one or more indirect methods (e.g., mass spectrometry).

Computational methods for ligand design are becoming more robust, and for certain immunogen-design applications, they are likely to be valuable[103]. It is anticipated that for the epitopes presented by HIV Env, however, the available structural information may be too restricted to allow one to rely primarily on a computational approach. The area of the interface between an antibody and a tightly-bound antigen is generally between 750 and 1000 Å$^2$, and on the surface of gp120, for example, such an interface might include several loops from different segments of the polypeptide chain. Even if both the structure of the mature-antibody:Env complex and that of the UA were known, computational design of a modified Env with enhanced affinity for the UA would be challenging. Selection approaches should, in the near term at least, be more satisfactory and more reliable.

For continuous epitopes, phage display is a well-developed selection method for finding high-affinity peptides[104]. The best-studied continuous epitopes on HIV Env are those for the antibodies, 2F5 and 4E10, directed against the membrane proximal external region (MPER) of gp41. Efforts to obtain neutralizing antibodies by immunization with peptides bearing the sequence of these epitopes have been generally unsuccessful, presumably in part because the peptide, even if cyclized, adopts only rarely the conformation required for recognition in the context of gp41. In a computational effort to design suitable immunogens, the 2F5 epitope was grafted onto computationally selected protein scaffolds that present the peptide epitope in the conformation seen in its complex with the 2F5 antibody. These immunogens indeed elicited guinea-pig antibodies that recognize the epitope in its presented conformation[105]. The MPER epitopes are exposed only on the fusion intermediate conformation of gp41, however, not on the prefusion trimer[106], and to have neutralizing activity, these antibodies must have a membrane-targeting segment at the tip of their heavy-chain CDR3 in addition to a high-affinity site for the peptide epitope[107]. Thus, more complex immunogens (e.g., coupled to some sort of membrane surface) may be necessary to elicit antibodies that have both properties.

Differences between antibody 2F5 and its probable unmutated ancestor have been mapped onto the 2F5 Fab:peptide-epitope complex. The side chains on the peptide that contact the antibody are all within a ten-residue stretch, and several of these (a DKW sequence in particular) must clearly be an anchor segment even for a complex with the UA. Randomization of no more than 5 positions in the peptide would cover contacts with all the residues in the UA that are different from their counterparts in the mature antibody. Phage display libraries can accommodate this extent of sequence variation (i.e., about 3×10⁶ members), so a direct lineage-based, experimental approach to finding potential immunogens is possible, by selecting from such libraries peptides that bind the UCA of a lineage or one of the inferred intermediates.

Figure 4:
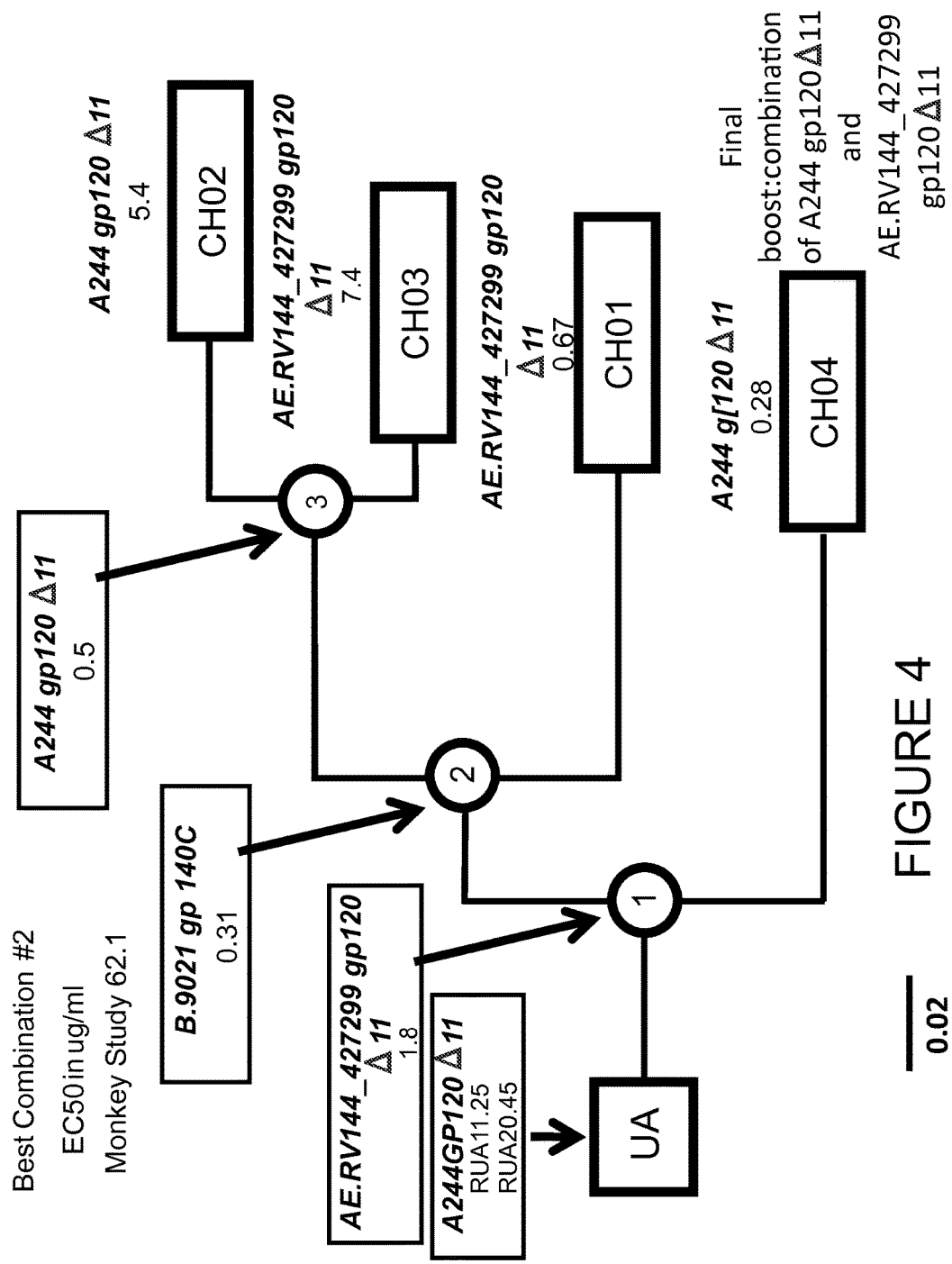
FIG. 4. Monkey study 62.1.
Figure 5:
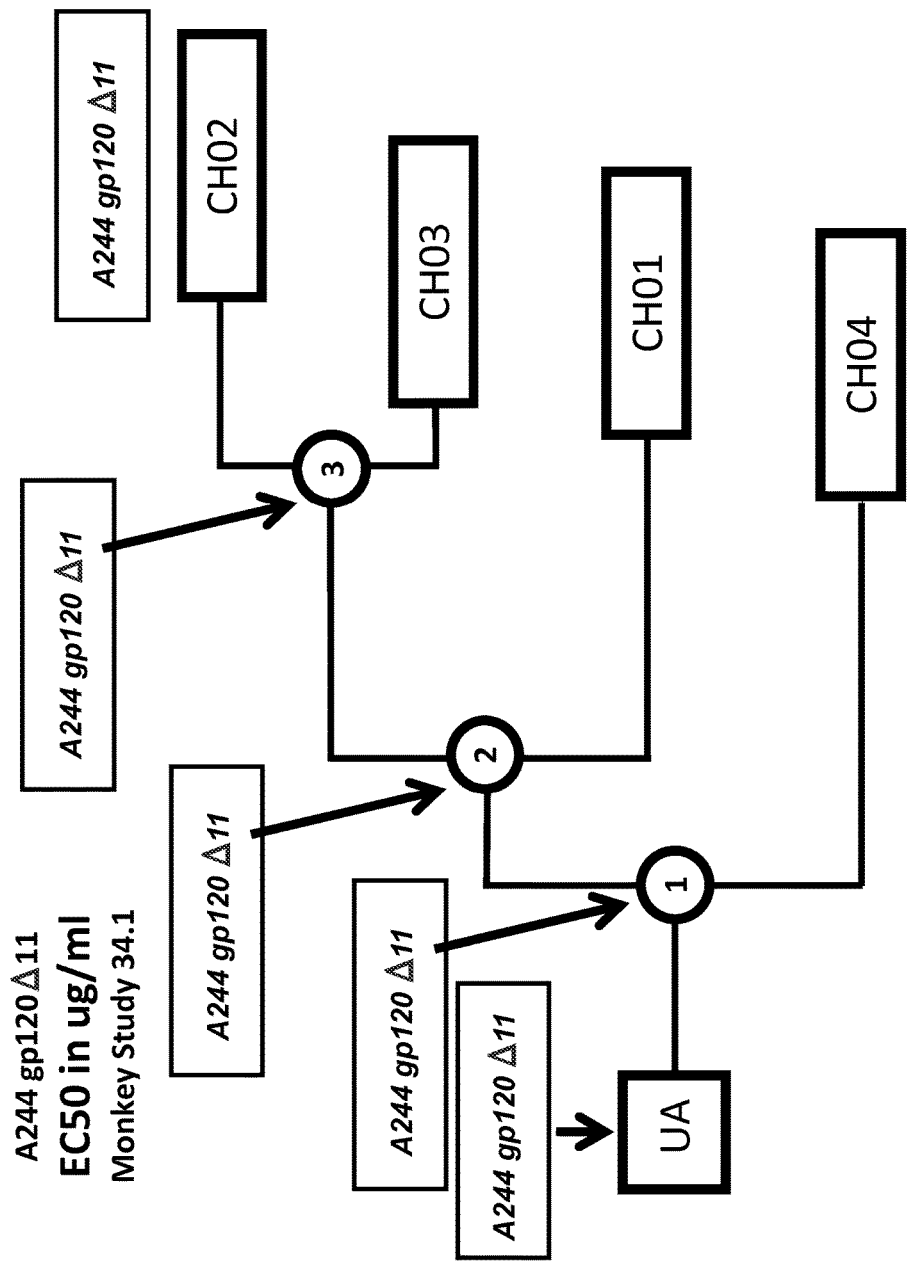
FIG. 5. Monkey study 34.1.
Figure 6:
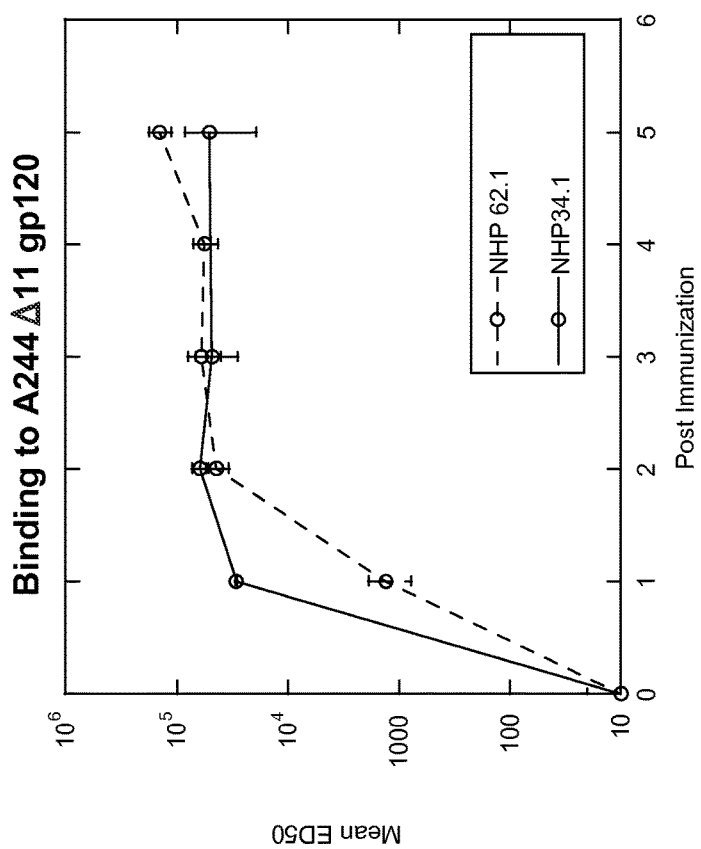
FIG. 6. Levels of binding antibodies to A244 gp120D11 induced by A244gp120D11 alone (NHP #34.1) and sequential Env immunization (NHP #62.1).
Figure 7:
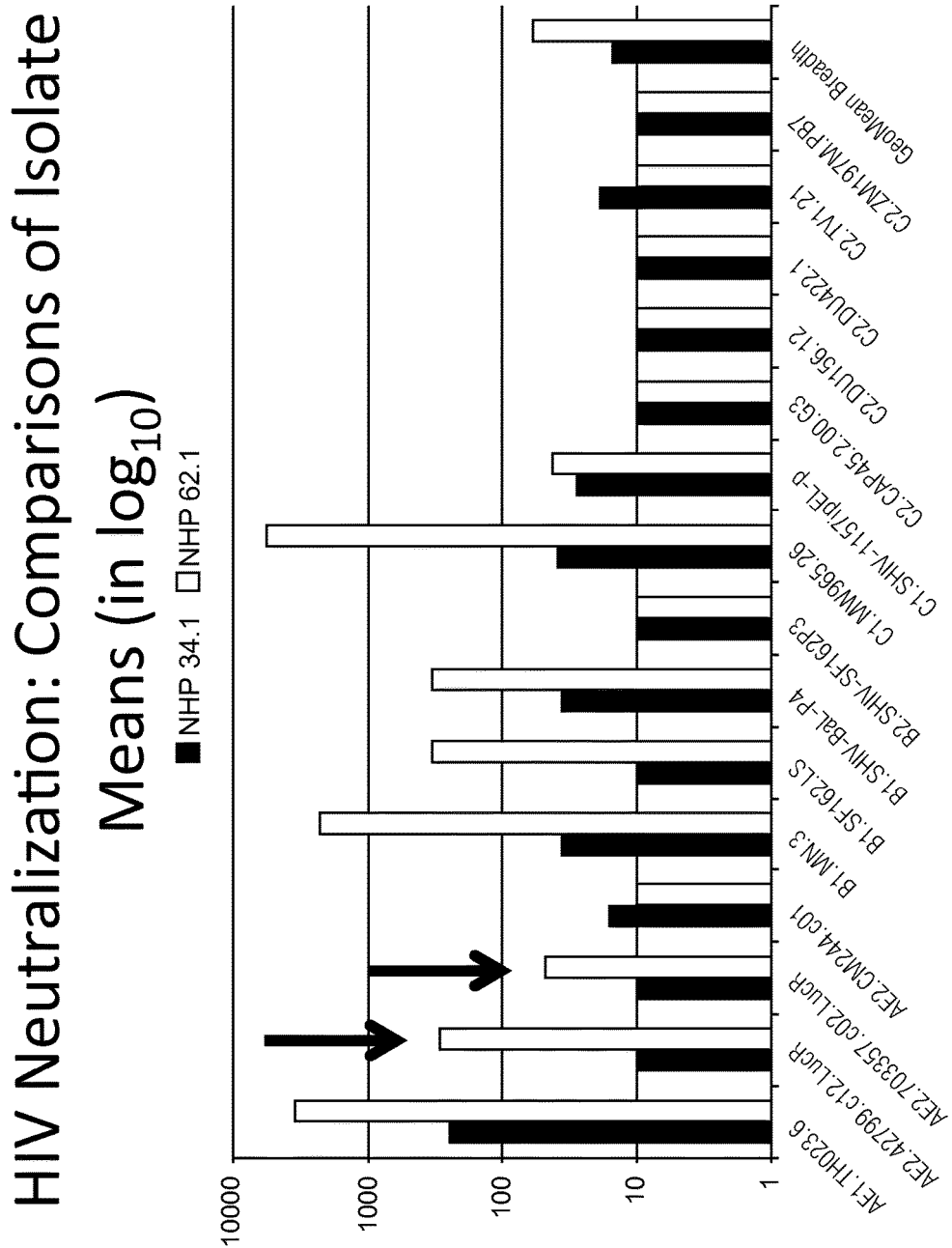
FIG. 7. HIV neutralization: comparisons of isolate means (in $\log_{10}$).

For discontinuous epitopes on gp120 that are antigenic on cell-surface expressed, trimeric Env, a selection scheme for variant Envs can be devised based on the same kind of single-cell sorting and subsequent sequencing used to derive the antibodies. Cells can be transfected with a library of Env-encoding vectors selectively randomized at a few positions, and the tag used for sorting can be, for example, be a fluorescently labeled version of the UA antibody. An appropriate procedure can be used to select only those cells expressing an Env variant with high affinity for the antibody. In cases for which a comparison has been made of the inferred UA sequence with the structure of an antigen-Fab complex, partial randomization of residue identities at 3-5 positions, as in the linear-epitope example, can be expected to generate the compensatory changes one is seeking.

Recognition of HIV-1 envelope by several classes of broadly neutralizing antibodies includes glycans presented by conformational protein epitopes. Such antibodies account for ~25% of the broadly neutralizing activity in the plasma of subjects selected for broad activity[108, 109]. By analogy with selection from phage-displayed libraries, synthetic libraries of glycans or peptide-glycan complexes can be screened to select potential immunogens with high affinity for UAs and IAs of clonal lineages[110]. Large-scale synthesis of chosen glycoconjugates can then yield the bulk material for immunization trials[111, 112].

The various approaches described herein are equally applicable to influenza-virus vaccine design. On the influenza-virus hemagglutinin (HA), two conserved epitopes have received recent attention—one, a patch that covers the fusion peptide on the "stem" of the elongated HA trimer[97, 98, 113], the other, the pocket for binding sialic acid, the influenza-virus receptor[114]. Screens of three phage-displayed libraries of human antibodies, each from a quite different source, yielded similar antibodies directed against the stem epitope, and additional human mAbs of this kind have been identified subsequently by B-cell sorting. Conservation of the stem epitope may be partly a consequence of low exposure, due to tight packing of HA on the virion surface, and hence low immunogenicity on intact virus particles. An antibody from a vaccinated subject that binds the sialic-acid binding pocket and that mimics most of the sialic-acid contacts has been characterized[114]. It neutralizes a very broad range of H1 seasonal strains.

In summary, HIV-1 is a paradigm for a number of viruses that acquire resistance to immune detection by rapid mutation of exposed epitopes. These viruses do have conserved sites on their envelope proteins but a variety of mechanisms prevent efficient induction by vaccines of antibodies to these conserved epitopes. Some of these mechanisms, at least in the case of HIV-1, appear to be properties of tolerance control in the immune system. It is, therefore, clear that conventional immunization strategies will not succeed. Only rarely does the B-cell response follow the affinity maturation pathways that give rise to HIV-1 or influenza broadly neutralizing antibodies, and until recently there were no technologies available to define the maturation pathways of a particular antibody type or specificity. With recombinant antibody technology, clonal memory B-cell cultures, and 454 deep sequencing, clonal lineages of broadly neutralizing antibodies can now be detected and analyzed. Immunogens can be optimized for high affinity binding to antibodies (B-cell receptors of clonal lineage B-cells) at multiple stages of clonal lineage development, by combining analysis of these lineages with structural analysis of the antibodies and their ligands. This combination provides a viable strategy for inducing B-cell maturation along pathways that would not be taken in response to conventional, single-immunogen vaccines.

Certain aspects of the present invention are described in greater detail in the non-limiting Example that follows.

Example 1

FIG. 4 shows the set of immunizations in NHP study 62.1 wherein immunogens were chosen based on how well they bound to the antibody members of the CH01-CH04 broad neutralizing clonal lineage. A244 gp120 delta 11 was used as the prime and the boost was the placebo breakthrough infection in the RV144 trial, 427299.AE gp120 env delta 11, then a further boost with the 9021.B gp140Cenv (but could have been delta 11 gp120—either one), another boost with A244 gp120 Env delta 11 and then another boost with a combination of A244 gp120 delta 11+427299 Env. As shown in FIG. 6, when the NHP study 34.1, in which A244 gp120 delta 11 alone was used (see FIG. 5)), was compared to NHP study 62.1, in terms of binding of antibodies to A244 gp120 delta 11, similar binding titers are observed. However, the comparison shown in FIG. 7 yields a completely different result. The blue neutralizing antibody levels are with A244 gp120 D11 Env (study 34.1) and are what was seen in the plasma of the RV144 trial (Montefiori et al, J. Inf. Dis. 206:431-41 (2012)) high titers to the tier 1 AE isolate that was in the vaccine AE92TH023, some other low level tier 1 neutralizing antibody levels, and the rest of the levels were negative (neutralizing antibody assay levels in this assay start at a plasma dilution of 1:20 such that levels on the graph of "10" are below the level of detection and are read as negative). In contrast, the titers to the tier 1s in the red bars from study 62.1 show 1-2 logs higher abs to the tier 1s but most importantly now significant neutralizing antibody levels to the two tier 2 transmitted founder breakthrough viruses from the RV144 trial (all assays in TZMBL assay, except for the two arrows indicate HIV isolates which were assayed in the A3R5 cell neutralizing antibody assay). Thus, by immunizing with sequential Envs chosen for their ability to optimally bind at UCA, IA and mature antibody member points of a broad neutralizing antibody lineage, the breadth of neutralizing antibody coverage has been increased by inducing new neutralizing antibodies to Tier 2 (difficult to neutralize) HIV strains AE.427299 and AE.703357, demonstrating proof of concept that the strategy of B cell lineage immunogen design can indeed induce improved neutralizing antibody breadth. Moreover, these data demonstrate a new discovery as a strategy for inducing greater breadth of neutralization in using the ALVAC/AIDSVAX type of vaccine (Haynes et al, NEJM 366: 1275-1286 (2012)) for future vaccine trials, and that is adding gp120 Envs to the primer and or the boost regimen made up of Env gp120s chosen from the breakthrough infections that did not match the original vaccine in RV144 to increase the potency of vaccine efficacy of a vaccine in Thailand. Rolland has shown that if the RV144 trial breakthrough viruses are compared from vaccinees and placebo recipients, those viruses that had similarity at the V2 region were controlled by 45% vaccine efficacy (Rolland M et al, Nature September 10, Epub ahead of print, doi: 10.1038/nature 11519, 2012). Thus, screening the sequences of RV144 breakthrough viruses for the most common HIV strains with Env V2 regions that did not match the vaccine should demonstrate the Env V2 motifs that should be included in additional prime or boosting Envs in the next vaccine to increase the vaccine efficacy. In addition, the adjuvant used will be important. In the trials above in NHP study 34.1 and 62.1 the adjuvant used was a squalene based adjuvant with TLR7+TLR9 agonists added to the squalene (see PCT/US2011/062055). Currently available adjuvants that are available and can be considered for use in humans is MF-59 (Dell'Era et al, Vaccine 30: 936-40 (2012)) or AS01B (Leroux-Roels et al, Vaccine 28: 7016-24 (2010)). Thus, a vaccine can be designed based on a polyvalent immunogen comprising a mixture of Envs administered in sequence as shown, for example, in FIG. 4 or alternatively the sequentially chosen Envs can be administered all together for each immunization as describe (Haynes et al, AIDS Res. Human Retrovirol. 11:211-21 (1995)) to overcome any type of primer-induce suppression of Env responses. Thus, the present invention relates, at least in part, to an approach to improving the RV144 vaccine by adding gp120s or gp140Cs (with or without the delta 11 (D11) deletion) (e.g., 427299 Env gp120 sequences) to the A244 gp120 immunogen to expand the coverage of the RV144 original vaccine. (See, for example FIGS. 4 and 5.) It can be seen that this strategy of probing the breakthrough viruses of any partially successful vaccine trial can utilize this strategy to improve that vaccines coverage of infectious agent strains and in doing so, improve the vaccine efficacy of that vaccine.

The present invention also relates in part to demonstrating proof of concept of the general strategy of vaccine design known as "B Cell Lineage Immunogen Design" wherein the prime and boost immunogens are chosen based on the strength of binding of each vaccine component to an antibody template in the antibody clonal lineage that is desired to induce.

All documents and other information sources cited herein are hereby incorporated in their entirety by reference. Also incorporated by reference is U.S. Provisional Application No. 61/542,469, filed Oct. 3, 2011 and International Application No. PCT/US2011/000352, filed Feb. 25, 2011.

REFERENCES

1. Hilleman, M. R. Overview of the needs and realities for developing new and improved vaccines in the 21st century. *Intervirology* 45, 199-211 (2002).
2. Plotkin, S. A. Vaccines: the fourth century. *Clin Vaccine Immunol* 16, 1709-1719 (2009).
3. Plotkin, S. A. Vaccines: correlates of vaccine-induced immunity. *Clin Infect Dis* 47, 401-409 (2008).
4. Plotkin, S. A. Correlates of protection induced by vaccination. *Clin Vaccine Immunol* 17, 1055-1065 (2010).
5. McElrath, M. J. & Haynes, B. F. Induction of immunity to human immunodeficiency virus type-1 by vaccination. *Immunity* 33, 542-554 (2010).
6. Thomas, S. J. & Endy, T. P. Critical issues in dengue vaccine development. *Curr Opin Infect Dis* 24, 442-450 (2011).
7. Halliday, J., Klenerman, P. & Barnes, E. Vaccination for hepatitis C virus: closing in on an evasive target. *Expert Rev Vaccines* 10, 659-672 (2011).
8. Nabel, G. J. & Fauci, A. S. Induction of unnatural immunity: prospects for a broadly protective universal influenza vaccine. *Nat Med* 16, 1389-1391 (2010).
9. Burton, D. R., Stanfield, R. L. & Wilson, I. A. Antibody vs. HIV in a clash of evolutionary titans. *Proc Natl Acad Sci USA* 102, 14943-14948 (2005).
10. Walker, B. D. & Burton, D. R. Toward an AIDS vaccine. *Science* 320, 760-764 (2008).
11. Verkoczy, L., Kelsoe, G., Moody, M. A. & Haynes, B. F. Role of immune mechanisms in induction of HIV-1 broadly neutralizing antibodies. *Curr Opin Immunol* 23, 383-390 (2011).
12. Xiao, X., Chen, W., Yang, F. & Dimitrov, D. S. Maturation pathways of cross-reactive HIV-1 neutralizing antibodies. *Viruses* 1, 802-817 (2009).
13. Dimitrov, D. S. Therapeutic antibodies, vaccines and antibodyomes. *MAbs* 2, 347-356 (2010).
14. Ma, B.-J. et al. Envelope deglycosylation enhances antigenicity of HIV-1 gp41 epitopes for both broad neutralizing antibodies and their unmutated ancestor antibodies. *PLoS Pathog* 7(9), e1002200 (2011).
15. Dal Porto, J. M., Haberman, A. M., Shlomchik, M. J. & Kelsoe, G. Antigen drives very low affinity B cells to become plasmacytes and enter germinal centers. *J Immunol* 161, 5373-5381 (1998).
16. Dal Porto, J. M., Haberman, A. M., Kelsoe, G. & Shlomchik, M. J. Very low affinity B cells form germinal centers, become memory B cells, and participate in secondary immune responses when higher affinity competition is reduced. *J Exp Med* 195, 1215-1221 (2002).
17. Shih, T., Meffre, E., Roederer, M. & Nussenzweig, M. Role of BCR affinity in T cell dependent antibody responses in vivo. *Nat Immunol* 3, 570-575 (2002).
18. Schwickert, T. A. et al. A dynamic T cell-limited checkpoint regulates affinity-dependent B cell entry into the germinal center. *J Exp Med* 208, 1243-1252 (2011).
19. Xiao, X. et al. Germline-like predecessors of broadly neutralizing antibodies lack measurable binding to HIV-1 envelope glycoproteins: implications for evasion of immune responses and design of vaccine immunogens. *Biochem Biophys Res Commun* 390, 404-409 (2009).
20. Liao, H. X. et al. Initial antibodies binding to HIV-1 gp41 in acutely infected subjects are polyreactive and highly mutated. *J Exp Med* (in press) (2011).
21. Alam, S. M. et al. Differential reactivity of germline allelic variants of a broadly neutralizing HIV-1 antibody to a gp41 fusion intermediate conformation. *J Virol* epub ahead of print, Sep. 14, 2011.
22. Bonsignori, M. et al. Analysis of a Clonal Lineage of HIV-1 Envelope V2/V3 Conformational Epitope-Specific Broadly Neutralizing Antibodies and Their Inferred Unmutated Common Ancestors. *J Virol* 85, 9998-10009 (2011).
23. Wu. X. et al. Focused Evolution of HIV-1 Neutralizing Antibodies Revealed by Structures and Deep Sequencing. *Science* epub ahead of print, Aug. 11, 2011.
24. Hardy, R. R., Carmack, C. E., Shinton, S. A., Kemp, J. D. & Hayakawa, K. Resolution and characterization of pro-B and pre-pro-B cell stages in normal mouse bone marrow. *J Exp Med* 173, 1213-1225 (1991).
25. Li, Y. S., Hayakawa, K. & Hardy, R. R. The regulated expression of B lineage associated genes during B cell differentiation in bone marrow and fetal liver. *J Exp Med* 178, 951-960 (1993).
26. Alt, F. W. et al. Ordered rearrangement of immunoglobulin heavy chain variable region segments. *EMBO J* 3, 1209-1219 (1984).
27. Ehlich, A., Martin, V., Muller, W. & Rajewsky, K. Analysis of the B-cell progenitor compartment at the level of single cells. *Curr Biol* 4, 573-583 (1994).

28. Karasuyama, H., Kudo, A. & Melchers, F. The proteins encoded by the VpreB and lambda 5 pre-B cell-specific genes can associate with each other and with mu heavy chain. *J Exp Med* 172, 969-972 (1990).
29. Karasuyama, H., Rolink, A. & Melchers, F. A complex of glycoproteins is associated with VpreB/lambda 5 surrogate light chain on the surface of mu heavy chain-negative early precursor B cell lines. *J Exp Med* 178, 469-478 (1993).
30. Goldsby, R. A., Kindt, T. J., Osborne, B. A. & Kuby, J. J. Immunology *Edn. Fifth*. (W. H. Freeman and Company, New York Edn. Fifth. (W. H. Freeman and Company, New York (2003).
31. Karasuyama, H., Rolink, A. & Melchers, F. Surrogate light chain in B cell development. *Adv Immunol* 63, 1-41 (1996).
32. Lin, W. & Desiderio, S. Regulation of V(D)J recombination activator protein RAG-2 by phosphorylation. *Science* 260, 953-959 (1993).
33. Li, Z., Dordai, D. I., Lee, J. & Desiderio, S. A conserved degradation signal regulates RAG-2 accumulation during cell division and links V(D)J recombination to the cell cycle. *Immunity* 5, 575-589 (1996).
34. Reth, M., Petrac, E., Wiese, P., Lobel, L. & Alt, F. W. Activation of V kappa gene rearrangement in pre-B cells follows the expression of membrane-bound immunoglobulin heavy chains. *EMBO J* 6, 3299-3305 (1987).
35. Schlissel, M. S. & Baltimore, D. Activation of immunoglobulin kappa gene rearrangement correlates with induction of germline kappa gene transcription. *Cell* 58, 1001-1007 (1989).
36. Alt, F. W., Blackwell, T. K. & Yancopoulos, G. D. Development of the primary antibody repertoire. *Science* 238, 1079-1087 (1987).
37. Rajewsky, K. Clonal selection and learning in the antibody system. *Nature* 381, 751-758 (1996).
38. Hardy, R. R. & Hayakawa, K. B cell development pathways. *Annu Rev Immunol* 19, 595-621 (2001).
39. Nemazee, D. & Weigert, M. Revising B cell receptors. *J Exp Med* 191, 1813-1817 (2000).
40. Wardemann, H. et al. Predominant autoantibody production by early human B cell precursors. *Science* 301, 1374-1377 (2003).
41. Wardemann, H. & Nussenzweig, M. C. B-cell self-tolerance in humans. *Adv Immunol* 95, 83-110 (2007).
42. Perez-Andres, M. et al. Human peripheral blood B-cell compartments: a crossroad in B-cell traffic. *Cytometry B Clin Cytom* 78 Suppl 1, S47-60 (2010).
43. Nemazee, D. A. & Burki, K. Clonal deletion of B lymphocytes in a transgenic mouse bearing anti-MHC class I antibody genes. *Nature* 337, 562-566 (1989).
44. Chen, C. et al. Deletion and editing of B cells that express antibodies to DNA. *J Immunol* 152, 1970-1982 (1994).
45. Adams, E., Basten, A. & Goodnow, C. C. Intrinsic B-cell hyporesponsiveness accounts for self-tolerance in lysozyme/anti-lysozyme double-transgenic mice. *Proc Natl Acad Sci USA* 87, 5687-5691 (1990).
46. Goodnow, C. C. Transgenic mice and analysis of B-cell tolerance. *Annu Rev Immunol* 10, 489-518 (1992).
47. Wardemann, H., Hammersen, J. & Nussenzweig, M. C. Human autoantibody silencing by immunoglobulin light chains. *J Exp Med* 200, 191-199 (2004).
48. Tiegs, S. L., Russell, D. M. & Nemazee, D. Receptor editing in self-reactive bone marrow B cells. *J Exp Med* 177, 1009-1020 (1993).
49. Radic, M., Erikson, J., Litwin, S. & Weigert, M. B lymphocytes may escape tolerance by revising their antigen receptors. *J Exp Med* 177, 1165-1173 (1993).
50. ten Boekel, E., Melchers, F. & Rolink, A. G. Changes in the V(H) gene repertoire of developing precursor B lymphocytes in mouse bone marrow mediated by the pre-B cell receptor. *Immunity* 7, 357-368 (1997).
51. Rolink, A. G., Andersson, J. & Melchers, F. Characterization of immature B cells by a novel monoclonal antibody, by turnover and by mitogen reactivity. *Eur J Immunol* 28, 3738-3748 (1998).
52. Tsuiji, M. et al. A checkpoint for autoreactivity in human IgM+ memory B cell development. *J Exp Med* 203, 393-400 (2006).
53. Meffre, E. et al. Surrogate light chain expressing human peripheral B cells produce self-reactive antibodies. *J Exp Med* 199, 145-150 (2004).
54. Carsetti, R., Kohler, G. & Lamers, M. C. Transitional B cells are the target of negative selection in the B cell compartment. *J Exp Med* 181, 2129-2140 (1995).
55. Loder, F. et al. B cell development in the spleen takes place in discrete steps and is determined by the quality of B cell receptor-derived signals. *J Exp Med* 190, 75-89 (1999).
56. Wang, H. et al. Transitional B cells lose their ability to receptor edit but retain their potential for positive and negative selection. *J Immunol* 179, 7544-7552 (2007).
57. Hayakawa, K. et al. Positive selection of natural autoreactive B cells. *Science* 285, 113-116 (1999).
58. Gu, H., Tarlinton, D., Muller, W., Rajewsky, K. & Forster, I. Most peripheral B cells in mice are ligand selected. *J Exp Med* 173, 1357-1371 (1991).
59. Levine, M. H. et al. A B-cell receptor-specific selection step governs immature to mature B cell differentiation. *Proc Natl Acad Sci USA* 97, 2743-2748 (2000).
60. Haynes, B. F. et al. Cardiolipin polyspecific autoreactivity in two broadly neutralizing HIV-1 antibodies. *Science* 308, 1906-1908 (2005).
61. Verkoczy, L. et al. Autoreactivity in an HIV-1 broadly reactive neutralizing antibody variable region heavy chain induces immunologic tolerance. *Proc Natl Acad Sci USA* 107, 181-186 (2010).
62. Verkoczy, L. et al. Rescue of HIV-1 Broad Neutralizing antibody-expressing B cells in 2F5 VH/VL Knockin Mice reveals multiple tolerance controls. *J. Immunol.* 187, 3785-3797 (2011).
63. Phillips, R. S. Structure, mechanism, and substrate specificity of kynureninase. *Biochim Biophys Acta* (2010).
64. Shlomchik, M. et al. Anti-DNA antibodies from autoimmune mice arise by clonal expansion and somatic mutation. *J Exp Med* 171, 265-292 (1990).
65. Tiller, T. et al. Autoreactivity in human IgG+ memory B cells. *Immunity* 26, 205-213 (2007).
66. Mietzner, B. et al. Autoreactive IgG memory antibodies in patients with systemic lupus erythematosus arise from nonreactive and polyreactive precursors. *Proc Natl Acad Sci USA* 105, 9727-9732 (2008).
67. Victora, G. D. et al. Germinal center dynamics revealed by multiphoton microscopy with a photoactivatable fluorescent reporter. *Cell* 143, 592-605 (2010).
68. Clarke, S. H. et al. Inter- and intraclonal diversity in the antibody response to influenza hemagglutinin. *J Exp Med* 161, 687-704 (1985).

69. Clarke, S. H. et al. V region gene usage and somatic mutation in the primary and secondary responses to influenza virus hemagglutinin. *J Immunol* 144, 2795-2801 (1990).
70. Pulendran, B., Kannourakis, G., Nouri, S., Smith, K. G. & Nossal, G. J. Soluble antigen can cause enhanced apoptosis of germinal-centre B cells. *Nature* 375, 331-334 (1995).
71. Shokat, K. M. & Goodnow, C. C. Antigen-induced B-cell death and elimination during germinal-centre immune responses. *Nature* 375, 334-338 (1995).
72. Han, S., Zheng, B., Dal Porto, J. & Kelsoe, G. In situ studies of the primary immune response to (4-hydroxy-3-nitrophenyl)acetyl. IV. Affinity-dependent, antigen-driven B cell apoptosis in germinal centers as a mechanism for maintaining self-tolerance. *J Exp Med* 182, 1635-1644 (1995).
73. Batista, F. D. & Neuberger, M. S. Affinity dependence of the B cell response to antigen: a threshold, a ceiling, and the importance of off-rate. *Immunity* 8, 751-759 (1998).
74. Zhang, J. & Shakhnovich, E. I. Optimality of mutation and selection in germinal centers. *PLoS Comput Biol* 6, e1000800 (2010).
75. Kepler, T. B. & Perelson, A. S. Somatic hypermutation in B cells: an optimal control treatment. *J Theor Biol* 164, 37-64 (1993).
76. Wrammert, J. et al. Rapid cloning of high-affinity human monoclonal antibodies against influenza virus. *Nature* 453, 667-671 (2008).
77. Moody, M. et al. H3N2 Influenza Infection Elicits More Cross-reactive and Less Clonally Expanded Anti-hemagglutinin Antibodies Than Influenza Vaccination. *PLoS One* (in press) (2011).
78. Kelsoe, G. In situ studies of the germinal center reaction. *Adv Immunol* 60, 267-288 (1995).
79. Rogozin, I. B. & Kolchanov, N. A. Somatic hypermutagenesis in immunoglobulin genes: II. Influence of neighbouring base sequences on mutagenesis. *Biochimica et Biophysica Acta (BBA)—Gene Structure and Expression* 1171, 11-18 (1992).
80. Di Noia, J. M. & Neuberger, M. S. Molecular Mechanisms of Antibody Somatic Hypermutation. *Annual Review of Biochemistry* 76, 1-22 (2007).
81. Kepler, T. B. Codon bias and plasticity in immunoglobulins. *Molecular Biology and Evolution* 14, 637-643 (1997).
82. Crotty, S. Follicular helper CD4 T cells (TFH). *Annu Rev Immunol* 29, 621-663 (2011).
83. Tomaras, G. D. et al. Initial B-cell responses to transmitted human immunodeficiency virus type 1: virion-binding immunoglobulin M (IgM) and IgG antibodies followed by plasma anti-gp41 antibodies with ineffective control of initial viremia. *J Virol* 82, 12449-12463 (2008).
84. Wei, X. et al. Antibody neutralization and escape by HIV-1. *Nature* 422, 307-312 (2003).
85. Richman, D. D., Wrin, T., Little, S. J. & Petropoulos, C. J. Rapid evolution of the neutralizing antibody response to HIV type 1 infection. *Proc Natl Acad Sci USA* 100, 4144-4149 (2003).
86. Gray, E. S. et al. The neutralization breadth of HIV-1 develops incrementally over four years and is associated with CD4+ T cell decline and high viral load during acute infection. *J Virol* 85, 4828-4840 (2011).
87. Hessell, A. J. et al. Fc receptor but not complement binding is important in antibody protection against HIV. *Nature* 449, 101-104 (2007).
88. Hessell, A. J. et al. Broadly neutralizing human anti-HIV antibody 2G12 is effective in protection against mucosal SHIV challenge even at low serum neutralizing titers. *PLoS Pathog* 5, e1000433 (2009).
89. Hessell, A. J. et al. Effective, low-titer antibody protection against low-dose repeated mucosal SHIV challenge in macaques. *Nature Med* 15, 951-954 (2009).
90. Hessell, A. J. et al. Broadly neutralizing monoclonal antibodies 2F5 and 4E10 directed against the human immunodeficiency virus type 1 gp41 membrane-proximal external region protect against mucosal challenge by simian-human immunodeficiency virus SHIVBa-L. *J Virol* 84, 1302-1313 (2010).
91. Scheid, J. F. et al. Broad diversity of neutralizing antibodies isolated from memory B cells in HIV-infected individuals. *Nature* 458, 636-640 (2009).
92. Gray, E. S. et al. Isolation of a monoclonal antibody that targets the alpha-2 helix of gp120 and represents the initial autologous neutralizing-antibody response in an HIV-1 subtype C-infected individual. *J Virol* 85, 7719-7729 (2011).
93. Walker, L. M. et al. Broad and potent neutralizing antibodies from an African donor reveal a new HIV-1 vaccine target. *Science* 326, 285-289 (2009).
94. Walker, L. M. et al. Broad neutralization coverage of HIV by multiple highly potent antibodies. *Nature* (Aug. 17, 2011).
95. Messmer, B. T. et al. Multiple distinct sets of stereotyped antigen receptors indicate a role for antigen in promoting chronic lymphocytic leukemia. *J Exp Med* 200, 519-525 (2004).
96. Tobin, G. et al. Subsets with restricted immunoglobulin gene rearrangement features indicate a role for antigen selection in the development of chronic lymphocytic leukemia. *Blood* 104, 2879-2885 (2004).
97. Throsby, M. et al. Heterosubtypic neutralizing monoclonal antibodies cross-protective against H5N1 and H1N1 recovered from human IgM+ memory B cells. *PLoS One* 3, e3942 (2008).
98. Sui, J. et al. Structural and functional bases for broad-spectrum neutralization of avian and human influenza A viruses. *Nat Struct Mol Biol* 16, 265-273 (2009).
99. Kashyap, A. K. et al. Combinatorial antibody libraries from survivors of the Turkish H5N1 avian influenza outbreak reveal virus neutralization strategies. *Proc Natl Acad Sci USA* 105, 5986-5991 (2008).
100. Zwick, M. B. et al. Broadly neutralizing antibodies targeted to the membrane-proximal external region of human immunodeficiency virus type 1 glycoprotein gp41. *J Virol* 75, 10892-10905 (2001).
101. Pancera, M. et al. Crystal structure of PG16 and chimeric dissection with somatically related PG9: structure-function analysis of two quaternary-specific antibodies that effectively neutralize HIV-1. *J Virol* 84, 8098-8110 (2010).
102. Changela, A. et al. Crystal structure of human antibody 2909 reveals conserved features of quaternary structure-specific antibodies that potently neutralize HIV-1. *J Virol* 85, 2524-2535 (2011).
103. Fleishman, S. J. et al. Computational design of proteins targeting the conserved stem region of influenza hemagglutinin. *Science* 332, 816-821 (2011).
104. Smith, G. P. & Petrenko, V. A. Phage Display. *Chem Rev* 97, 391-410 (1997).

105. Ofek, G. et al. Elicitation of structure-specific antibodies by epitope scaffolds. *Proc Natl Acad Sci USA* 107, 17880-17887 (2010).
106. Frey, G. et al. A fusion-intermediate state of HIV-1 gp41 targeted by broadly neutralizing antibodies. *Proc Natl Acad Sci USA* 105, 3739-3744 (2008).
107. Alam, S. M. et al. Role of HIV membrane in neutralization by two broadly neutralizing antibodies. *Proc Natl Acad Sci USA* 106, 20234-20239 (2009).
108. Walker, L. M. et al. A limited number of antibody specificities mediate broad and potent serum neutralization in selected HIV-1 infected individuals. *PLoS Pathog* 6, e1001028 (2010).
109. Tomaras, G. D. et al. Polyclonal B cell responses to conserved neutralization epitopes in a subset of HIV-1 infected individuals. *J Virol* (in press) (Aug. 17, 2011).
110. Calarese, D. A. et al. Dissection of the carbohydrate specificity of the broadly neutralizing anti-HIV-1 antibody 2G12. *Proc Natl Acad Sci USA* 102, 13372-13377 (2005).
111. Wang, P. & Danishefsky, S. J. Promising general solution to the problem of ligating peptides and glycopeptides. *J Am Chem Soc* 132, 17045-17051 (2010).
112. Yuan, Y. et al. Toward homogeneous erythropoietin: fine tuning of the C-terminal acyl donor in the chemical synthesis of the Cys29-Gly77 glycopeptide domain. *J Am Chem Soc* 131, 5432-5437 (2009).
113. Ekiert, D. C. et al. Antibody recognition of a highly conserved influenza virus epitope. *Science* 324, 246-251 (2009).
114. Whittle, J. R. et al. Broadly neutralizing human antibody that recognizes the receptor-binding pocket of influenza virus hemagglutinin. *Proc Natl Acad Sci USA* 108, 14216-14221 (2011).

What is claimed is:

1. A method of inducing an immune response in a mammal comprising sequentially administering to said mammal a prime immunogen and a boost immunogen, wherein the prime immunogen comprises all the consecutive amino acids after signal peptide sequence MRVKETQMNWPNLWKWGTLILGLVIICSA in SEQ ID NO: 2 and wherein the boost immunogen comprises all the consecutive amino acids after signal peptide sequence MRVKGIRKNCQQHLWRWGTMLLGILMICSA in SEQ ID NO: 4.

2. A method of inducing an immune response in a mammal comprising sequentially administering to said mammal a prime immunogen and a boost immunogen, wherein the prime immunogen comprises all the consecutive amino acids after signal peptide sequence MRVKETQMNWPNLWKWGTLILGLVIICSA in SEQ ID NO: 2 and wherein the boost immunogen comprises all the consecutive amino acids after signal peptide sequence MRVKETQRSWPNLWKWGTLILGLVIMCNA in SEQ ID NO: 3.

3. The method of claim 1, further comprising administering at least one further boost immunogen.

4. The method of claim 3, wherein the further boost immunogen is selected from the group consisting of a boost immunogen comprising all the consecutive amino acids after signal peptide sequence MRVKETQMNWPNLWKWGTLILGLVIICSA in SEQ ID NO: 2, a boost immunogen comprising all the consecutive amino acids after signal peptide sequence MRVKETQRSWPNLWKWGTLILGLVIMCNA in SEQ ID NO: 3, and a boost immunogen comprising all the consecutive amino acids after signal peptide sequence MRVKGIRKNCQQHLWRWGTMLLGILMICSA in SEQ ID NO: 5.

5. The method of claim 2, further comprising administering at least one further boost immunogen.

6. The method of claim 5, wherein the further boost immunogen is selected from the group consisting of a boost immunogen comprising all the consecutive amino acids after signal peptide sequence MRYKETQMNWPNLWKWGTLILGLVIICSA in SEQ 2, a boost immunogen comprising all the consecutive amino acids after signal peptide sequence MRYKGIRKNCOOHLWRWGTMLLGILMICSA in SEQ ID NO: 4, and a boost immunogen comprising all the consecutive amino acids after signal peptide sequence MRVKGIRKNCOOHLWRWGTMLLGILMICSA in SEQ ID NO: 5.

7. The method of claim 6, further comprising administering all the consecutive amino acids after signal peptide sequence MRVKETQMNWPNLWKWGTLILGLVIICSA in SEQ ID NO: 2 and all the consecutive amino acids after signal peptide sequence MRVKETQRSWPNLWKWGTLILGLVIMCNA in SEQ ID NO: 3 as an additional further boost.

8. A composition comprising an immunogen comprising all the consecutive amino acids after signal peptide sequence MRVKETQMNWPNLWKWGTLILGLVIICSA in SEQ ID NO: 2 and an immunogen comprising all the consecutive amino acids after signal peptide sequence MRVKETQRSWPNLWKWGTLILGLVIMCNA in SEQ ID NO: 3.

9. The composition of claim 8, further comprising, an adjuvant.

10. The method of claim 4, further comprising administering all the consecutive amino acids after signal peptide sequence MRVKETQMNWPNLWKWGTLILGLVIICSA in SEQ ID NO: 2 and all the consecutive amino acids after signal peptide sequence MRVKETQRSWPNLWKWGTLILGLVIMCNA in SEQ ID NO: 3 as an additional further boost.

11. A method of inducing an immune response in a mammal comprising sequentially administering to said mammal a prime immunogen and a boost immunogen, wherein the prime immunogen comprises all the consecutive amino acids after signal peptide sequence MRVKETQMNWPNLWKWGTLILGLVIICSA in SEQ ID NO: 2 and wherein the boost immunogen comprises all the consecutive amino acids after signal peptide sequence MRVKGIRKNCQQHLWRWGTMLLGILMICSA in SEQ ID NO: 5.

12. The method of claim 11, further comprising administering at least one further boost immunogen.

13. The method of claim 12, wherein the further boost immunogens are selected from the group consisting of a boost immunogen comprising all the consecutive amino acids after signal peptide sequence MRVKETQMNWPNLWKWGTLILGLVIICSA in SEQ ID NO: 2, a boost immunogen comprising all the consecutive amino acids after signal peptide sequence MRVKETQRSWPNLWK- WGTLILGLVIMCNA in SEQ ID NO: 3, and a boost immunogen comprising all the consecutive amino acids after signal peptide sequence MRVKGIRKNCQQHLWRWGT-MLLGILMICSA in SEQ ID NO: 4.

14. The method of claim 13, further comprising administering all the consecutive amino acids after signal peptide sequence MRVKETQMNWPNLWKWGTLILGLVIICSA in SEQ ID NO: 2 and all the consecutive amino acids after signal peptide sequence MRVKETQRSWPNLWK-WGTLILGLVIMCNA in SEQ ID NO: 3 as an additional further boost.

15. The method of any of claims 1, 2-7, 10-14 further comprising administering an adjuvant.

16. The method of claim 15, wherein the adjuvant is a squalene-based adjuvant.

17. The method of claim 15, wherein the adjuvant further comprises TLR7 and TLR9 agonists.

* * * * *

UNITED STATES PATENT AND TRADEMARK OFFICE
CERTIFICATE OF CORRECTION

PATENT NO.         : 10,092,638 B2  
APPLICATION NO.    : 14/349539  
DATED              : October 9, 2018  
INVENTOR(S)        : Barton F. Haynes et al.

Page 1 of 1

It is certified that error appears in the above-identified patent and that said Letters Patent is hereby corrected as shown below:

In the Specification

After Column 1, Line 11, please insert:

--GOVERNMENT SUPPORT  
This invention was made with government support under Grant No. AI 067854 awarded by the National Institutes of Health. The government has certain rights in the invention.

SEQUENCE LISTING  
The instant application contains a Sequence Listing which has been submitted electronically in ASCII format and is hereby incorporated by reference in its entirety. Said ASCII copy, created on June 13, 2014, is named 1579-1959_SL.txt and is 19,991 bytes in size.--

Signed and Sealed this  
Fourth Day of June, 2019

Andrei Iancu  
*Director of the United States Patent and Trademark Office*